US008765954B2

(12) United States Patent
Adelman et al.

(10) Patent No.: US 8,765,954 B2
(45) Date of Patent: *Jul. 1, 2014

(54) 1,8-NAPHTHYRIDINE COMPOUNDS FOR THE TREATMENT OF CANCER

(75) Inventors: Daniel C. Adelman, Redwood City, CA (US); Marc J. Evanchik, San Jose, CA (US); Anantha Sudhakar, Fremont, CA (US); Jeffrey William Jacobs, San Mateo, CA (US); Jeffrey A. Silverman, Burlingame, CA (US)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/360,558

(22) Filed: Jan. 27, 2012

(65) Prior Publication Data

US 2012/0245198 A1 Sep. 27, 2012

Related U.S. Application Data

(63) Continuation of application No. 12/304,750, filed as application No. PCT/US2007/013873 on Jun. 12, 2007, now Pat. No. 8,124,773.

(60) Provisional application No. 60/812,835, filed on Jun. 12, 2006.

(51) Int. Cl.
C07D 471/04 (2006.01)
A61K 31/4375 (2006.01)

(52) U.S. Cl.
USPC .......................................... 546/123; 514/300

(58) Field of Classification Search
USPC .......................................... 546/123; 514/300
See application file for complete search history.

(56) References Cited

U.S. PATENT DOCUMENTS

| | | | |
|---|---|---|---|
| 4,261,989 A | 4/1981 | Sasaki et al. |
| 4,810,643 A | 3/1989 | Souza |
| 4,999,291 A | 3/1991 | Souza |
| 5,078,966 A | 1/1992 | Strong et al. |
| 5,134,127 A | 7/1992 | Stella et al. |
| 5,229,496 A | 7/1993 | Deeley et al. |
| 5,391,485 A | 2/1995 | Deeley et al. |
| 5,393,870 A | 2/1995 | Deeley et al. |
| 5,528,823 A | 6/1996 | Rudy, Jr. et al. |
| 5,580,755 A | 12/1996 | Souza |
| 5,817,669 A | 10/1998 | Tomita et al. |
| 6,171,857 B1 | 1/2001 | Hendrickson |
| 6,291,643 B1 | 9/2001 | Zou et al. |
| 6,570,002 B1 | 5/2003 | Hardwick et al. |
| 6,641,810 B2 | 11/2003 | Gold |
| 6,670,144 B1 | 12/2003 | Craig et al. |
| 6,696,483 B2 | 2/2004 | Singh |
| 6,723,734 B2 | 4/2004 | Kim et al. |
| 7,211,562 B2 | 5/2007 | Rosen et al. |
| 2003/0165887 A1 | 9/2003 | Reed |
| 2003/0216316 A1 | 11/2003 | Haran-Ghera et al. |
| 2005/0203120 A1 | 9/2005 | Adelman et al. |
| 2005/0215583 A1 | 9/2005 | Arkin et al. |
| 2006/0025437 A1 | 2/2006 | Adelman et al. |
| 2006/0063795 A1 | 3/2006 | Arkin et al. |
| 2006/0247267 A1 | 11/2006 | Adelman et al. |
| 2008/0063642 A1 | 3/2008 | Adelman et al. |

FOREIGN PATENT DOCUMENTS

| | | |
|---|---|---|
| JP | 09-221424 | 8/1997 |
| JP | 11-349565 | 12/1999 |
| WO | WO98/30902 | 7/1998 |
| WO | WO01/74395 | 10/2001 |
| WO | WO02/20500 | 3/2002 |
| WO | WO2004/085418 | 10/2004 |
| WO | WO2007/028171 | 3/2007 |
| WO | WO2007/146335 | 12/2007 |
| WO | WO2008/016678 | 2/2008 |
| WO | WO2009/054935 | 4/2009 |
| WO | WO2009/075841 | 6/2009 |

OTHER PUBLICATIONS

Krutoholow "Sunesis' voreloxin offers modest response rates, but encouraging toxicity in AML—Hematologists" Pharmawire May 19, 2010.*
Trisha Gura "Cancer Models: Systems for Identifying New Drugs Are Often Faulty" Science Nov. 7, 1997: vol. 278. No. 5340, pp. 1041-1042.*
Johnson, et. al. "Relationships between drug activity in NCI preclinical in vitro and in vivo models and early clinical trials." British Journal of Cancer 2001, 84, 1424-1431.*
Simone, Oncology: Introduction, Cecil Textbook of Medicine, 20th Edition, 1996 vol. 1, pp. 1004-1010.*
Allen, J.C., Database MEDLINE Accession No. 92345081, "Complications of Chemotherapy in Patients with Brain and Spinal Cord Tumors", Ped. Neurosurg., vol. 17, No. 4, pp. 218-224, 1991-1992.
Chiba, et al., "Practical Synthesis of AG-7352, Optically Active New Antitumor Agent." Abstract, 218th ACS National Meeting, Aug. 22-26, 1999.
Cleton, F.J., "History of the Development of Anticancer Drugs", Oxford Textbook of Oncology, vol. 1. pp. 445-453, 1995.
Emens, et al., Curr. Opinion Mol. Ther. 3(1):77-84, 2001.
Evanchik, et al., "Non-Clinical Admet, PK, and Biological Activity of SNS-595, a Novel Cell Cycle Inhibitory Antineoplastic Agent." Drug metabolism reviews, Marcel Dekker,New York, NY, US, vol. 36, No. SUPPL1, Aug. 2004 (2004-2008), p. 103.
Freireich, et al., "Quantitative Comparison of Toxicity of Anticancer Agents in Mouse, Rat, Hamster, Dog, Monkey, and Man", Cancer Chemotherapy Reports, vol. 50, No. 4, pp. 219-244, May 1966.

(Continued)

*Primary Examiner* — David K O Dell
(74) *Attorney, Agent, or Firm* — Jones Day

(57) ABSTRACT

Compounds and compositions for treating, preventing or managing cancer are disclosed. The compositions provided herein comprise SNS-595 and N-desmethyl-SNS-595. Also provided are pharmaceutical compositions comprising the compounds and methods of treatment using the compounds and compositions.

8 Claims, 10 Drawing Sheets

(56) References Cited

OTHER PUBLICATIONS

Glaspy, et al., "Database Cancer Lit Accession No. 2002-047630, A dose-Finding and Safety Study of Novel Erythropoiesis Stimulating Protein (NESP) for the Treatment of Anaemia in Patients Receiving Multicycle Chemotherapy", Br. J. Cancer, vol. 84 (Suppl. 1), pp. 17-23, Apr. 2001.
Herman, et al., Database MEDLINE Accession No. 78104303, "Nabilone: A Potent Antiemetic cannabinol with Minimal Euphoria", Biomedicine. Vo. 27, No. 9-10, pp. 331-334, Dec. 1977.
Jacobs, Leonard S., "National Medical Series for Independent Study: Pharmacology", Fourth Edition, Chapter 11, pp. 253-274, 1996.
Kashimoto, et al., Database BIOSIS Accession No. 2001:366681, "Antitumor Activity of a Novel Quinolone Analog AG-7352 in Human Xenograft Models of Leukemia or Drug-Resistant Tumors and in an Experimental Metastatic Tumor Model", Proc. Am. Assoc. Can. Res. An. Mtg., vol. 42, p. 102, Mar. 2001.
Lawrence, et al., "SNS-595, a Novel S-Phase Active Cytotoxic, Demonstrates Pharmacologic Properties Appropriate for the Treatment of Advanced Hematologic Malignancies." Blood, vol. 106, No. 11, Part 2, Nov. 2005, p. 2378.
Lawrence, et al., "SNS-595, A Novel S-Phase Active Cytotoxic, Exhibits Potent In Vitro and In Vivo Activities, and Has the Potential for Treating Advanced Hematoloic Malignacies." Proceedings of the Annual Meeting of the American Association for Cancer Research, New York, NY, vol. 47, Apr. 2006, p. 1110.
Ledwidge, et al., "Effects of surface active characteristics and solid state forms on the pH solubility profiles of drug-salt systems," International Journal of Pharmaceutics 174 (1998) 187-200.
The Merck Manual (1999), pp. 973-995.
Nakano, et al., "Antitumor Activity of a Novel Quinolone DNA Topoisomerase II Inhibitor AG-7352." Proceedings of the Annual Meeting of the American Association for Cancer Research, New York, NY, vol. 40, Mar. 1999, p. 115-Abstract 767. XP008073720.
Penichet, et al., "Antibody-cytokine fusion proteins for the therapy of cancer," J. Immunol. Methods 248:91-101, 2001.
Ryffel, B., Database Cancer Lit Accession No. 97254190, "Safety of Human Recombinant Proteins", Biomed. Environ. Sci. vol. 190, No. 1, pp. 65-72, Mar. 1997.
Sato, et al., "In Vivo Antitumor Activity of a Novel Quinolone Analogue AG-7352 Against a Borad-Spectrum of Cancers and Drug-Resistant Human Cancers." Abstract, 11th NCI-EOARTC-AACR symposium on new drugs in cancer therapy, Nov. 7-10, 2000.
Tiierasse, et al., "New Guidelines to Evaluate the Response to Treatment in Solid Tumors", Journal of the National Cancer Institute, Vo. 92, No. 3, Feb. 2, 2000.
Thirion, et al., "Interest of investigating p53 status in breast cancer by four different methods." Oncology Reports, vol. 9, No. 6, Nov. 2002, pp. 1167-1172.
Tolcher, et al., "Phase I and Pharmacokinetic Study of NSC 655649, a Rebeccamycin Analog with Topoisomerase Inhibitory Properties", Journal of Clinical Oncology, vol. 19, pp. 2937-2947, No. 11, Jun. 1, 2001.
Tomita, Synthesis and Structure-Activity Relationships of Novel 7-Substituted 1.4-Dihydro-4-oxo-1 -(2-thiazolyl)-1,8-naphthyridine-3-carboxylic Acids as Antitumor Agents, Part 1, J.Med.Chem. 2002, vol. 45, pp. 5564-5575, 2002.
Tomita, et al., Database CAPLUS Accession No. 1999:92763, "Synthesis and Antitumor activity of Novel 7-Substituted 1, 4-dihydro-4-oxo-1-2(2-thiazolyl)-1,8-naphthyridine-3-carobxylic Acids", BK Abstracts, 217th ACS Nat Mtd., Mar. 21-25, 1999.
Tsuzuki, et al., "Practical Synthesis of (3S,4S)-3-Methoxy-4-Methylaminopyrrolidine." Tetrahedron: Asymmetry 12(2001) 2989-2997.
Tsuzuki, et al., "Process Research of a Novel Quinolone Antitumor Agent, AG-7352." English Abstract, The Japanese Society for Process Chemstry, 2004 Summer Symposium.
Tsuzuki, et al., "Synthesis and Structure—Activity Relationships of 3-Substitued 1, 4-Dihydro-4-Oxo-1-(2-Thiazolyl)-1, 8-Naphthridines as Novel Antitumor Agents." Bioorganic & Medicinal Chemistry Letters 14 (2004): 3189-3193.
Tsuzuki, et al., "Synthesis of Optically Active Amine at C-7 Position of New Antitumor Agent AG-7352." Abstract, Molecular Chirality Conference, 1999.
Tsuzuki, et al., "Efficient stereospecific synthesis of (S,S)-3-methozy-4-methylaminopyrrolidine", Tetrahedron: Asymmetry, vol. 12, pp. 1793-1799, 2001.
Tsuzuki, et al., Synthesis and Structure-Activity Relationships of Novel 7-Substituted 1,4-Dihydro-4-oxo-1-(2-thiazolyl)-1,8-naphthyridine-3-carboxylic Acids as Antitumor Agents, Part 2, vol. 47, pp. 2097-2109, 2004.
Wright, et al., "SNS-595 Has Synergistic Activity in Vitro with DNA Damaging Agents and Antimetabolites." Proceedings of the Annual Meeting of the American Association for Cancer Research, New York, NY, vol. 47, Apr. 2006, p. 504. XP001199686.
U.S.P.T.O. non-Final Office Action dated Jul. 18, 2007 for U.S. Appl. No. 11/080,283, filed Mar. 14, 2005.
U.S.P.T.O. non-Final Office Action dated Mar. 24, 2008 for U.S. Appl. No. 11/080,283, filed Mar. 14, 2005.
U.S.P.T.O. Final Office Action dated Dec. 31, 2008 for U.S. Appl. No. 11/080,283, filed Mar. 14, 2005.
Goodman & Gilman, The Pharmacological Basis of Therapeutics, McGraw-Hill Medical Publishing Division, Tenth Edition, 2001, pp. 1404-1411.
Page, Do. Ph.D., "Principles of chemotherapy", Cancer Management: A Multidisciplinary Approach, Fifth Edition, 2001, pp. 21-28.

* cited by examiner

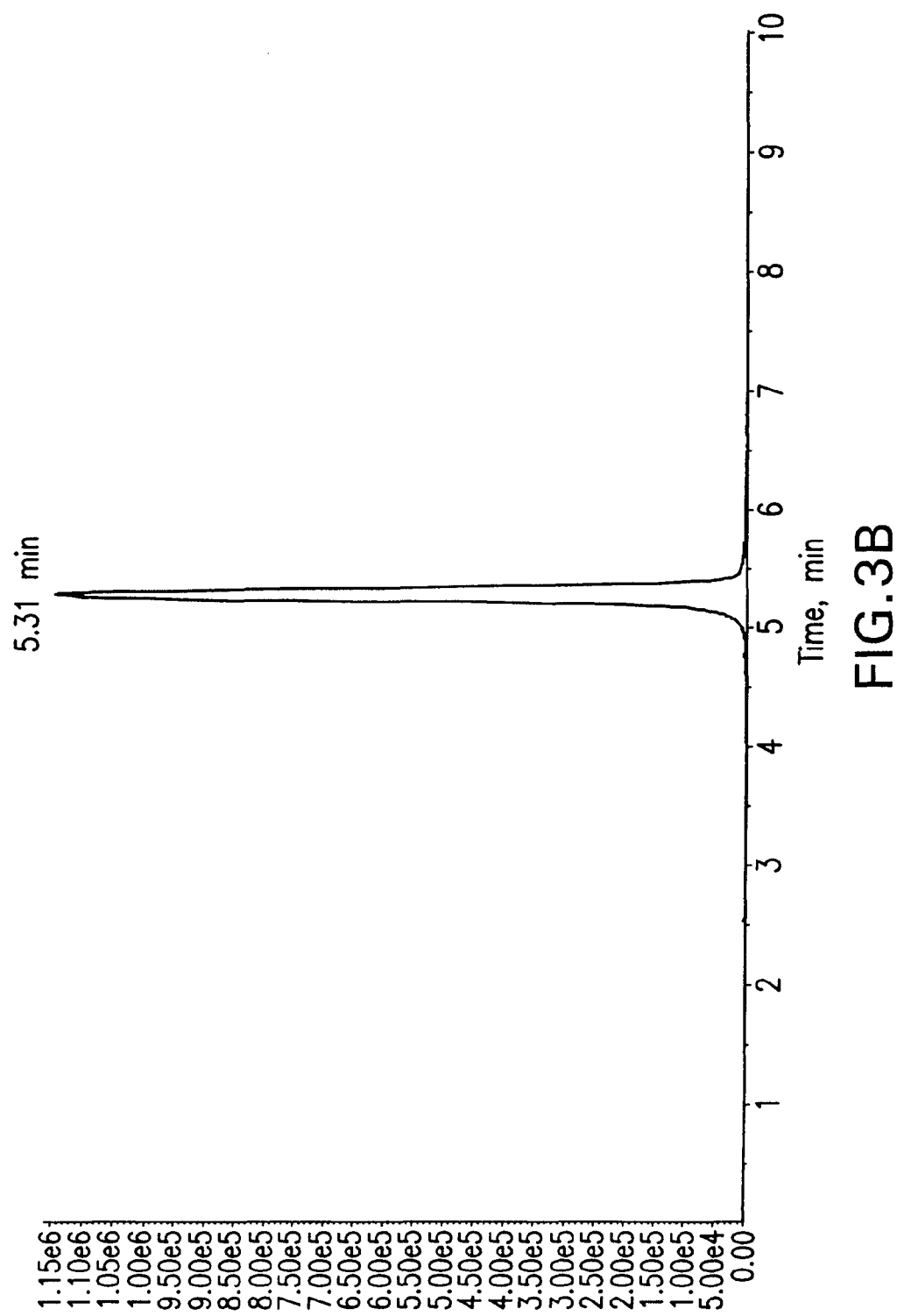

1,8-NAPHTHYRIDINE COMPOUNDS FOR THE TREATMENT OF CANCER

1. RELATED APPLICATIONS

This application is a continuation of U.S. application Ser. No. 12/304,750 filed Jun. 5, 2009 now U.S. Pat. No. 8,124,773, which is a 371 of PCT/US2007/013873, filed Jun. 12, 2007, which claims priority to U.S. provisional application Ser. No. 60/812,835, filed Jun. 12, 2006, entitled "Compounds And Compositions For Treatment Of Cancer". The disclosure of each of the above referenced application is incorporated by reference herein in its entirety.

2. FIELD

Provided herein are compounds, compositions and methods of their use for treatment of cancer. Compositions provided herein comprise, for example, (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and N-desmethyl(+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid.

3. BACKGROUND (+)-1,4-Dihydro-7-[(3S,4S)-3-methoxy-4-(methylamino)-1-pyrrolidinyl]-4-oxo-1-(2-thiazolyl)-1,8-naphthyridine-3-carboxylic acid is known for its anti-tumor activity (see, Tsuzuki et al., *J. Med. Chem.*, 47:2097-2106, 2004 and Tomita et al., *J. Med. Chem.*, 45: 5564-5575, 2002). Treatment of the following cancers with (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid has been proposed in the literature: bladder cancer, breast cancer, cervical cancer, colon cancer, esophageal cancer, head and neck cancer, liver cancer, lung cancer, melanoma, myeloma, neuroblastoma, ovarian cancer, pancreatic cancer, prostate cancer, renal cancer, sarcoma, skin cancer, stomach cancer, testicular cancer, thyroid cancer and uterine cancer. Various dosing regimens for the use of this compound have been reported, for example, see, U.S. Patent Application Pub. Nos. 2005-0203120; 2005-0215583 and 2006-0025437 and International Application No. PCT/US2006/034699, which are incorporated herein by reference in their entirety.

4. SUMMARY

In certain embodiments, provided herein are compositions comprising (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and N-desmethyl(+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid. In certain embodiments, the compositions provided herein comprise at least about 97% (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and from about 0.01% up to about 3% of N-desmethyl(+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid by total weight of the composition, wherein each of the percentage is based upon total weight of the two components.

In certain embodiments, the compositions are pharmaceutical compositions. In certain embodiments, the compositions provided herein can be synthesized on a process scale. In certain embodiment, the compositions are useful in the methods of treating, preventing or managing one or more cancers in a mammal.

In certain embodiments, provided herein is a compound selected from O-desmethyl(+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and a glucoranide of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid. In one embodiment, provided herein are pharmaceutical compositions comprising a compound selected from N-desmethyl(+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, O-desmethyl(+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and a glucoranide of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and methods of using the same for treating, preventing or managing one or more cancers.

In certain embodiments, the methods provided herein comprise administering N-desmethyl(+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid in the compositions or dosages described herein to treat, prevent and manage one or more cancers.

The types of cancers that can be treated, prevented or managed using methods provided herein include, but are not limited to solid tumors and blood born tumors. In certain embodiment, cancer can be cancer of skin tissues, organs, blood, and vessels, including, but not limited to, cancers of the bladder, bone or blood, brain, breast, cervix, chest, colon, endometrium, esophagus, eye, head, kidney, liver, lung, mouth, neck, ovaries, pancreas, prostate, rectum, stomach, testis, throat and uterus. In certain embodiment, the cancer is hematologic malignancy, such as leukemias, lymphomas (Non-Hodgkin's Lymphoma), Hodgkin's disease (also called Hodgkin's Lymphoma) and myeloma. In certain embodiments, the leukemia is chronic lymphocytic leukemia, chronic myeloid leukemia, acute lymphocytic leukemia, acute myelogenous leukemia and acute myeloblastic leukemia. In certain embodiments, the cancer comprises solid tumor. In certain embodiments, the cancer can be relapsed, refractory or resistant to conventional therapy. In certain embodiments, the cancer can be metastatic.

Also provided are methods of preparing the compositions and compounds described herein.

5. BRIEF DESCRIPTION OF FIGURES

FIG. 1 provides results of comparative cell viability assay using (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (squares), N-desmethyl(+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (inverted triangles) and O-desmethyl(+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (triangles).

FIG. 2 provides a scheme for the synthesis of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid.

FIG. 3 provides chromatograms of N-desmethyl(+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid produced after incubation in liver microsomes (pane A) and a separate aliquot from the same incubation with authentic N-desmethyl(+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid standard spiked in after the incubation was terminated (pane B).

FIG. 4 provides an HPLC chromatogram for the reaction products for an in vitro reaction of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid with human liver microsomes indicating two desmethyl products, N-desmethyl(+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and O-desmethyl(+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid. The chromatogram represents a 60 min incubation with 100 µM (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (major peak indicates product obtained in the reaction with NADPH and minor peak indicates product obtained in the reaction without NADPH).

FIG. 5 provides a product ion scan of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid with structures assigned to the major m/z fragments.

FIG. 6 provides a product ion scan of N-desmethyl(+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid with structures assigned to the major m/z fragments.

FIG. 7 provides an HPLC chromatogram for an exemplary composition comprising about 99.2% (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and about 0.6% N-desmethyl(+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid.

6. DETAILED DESCRIPTION

6.1 Definitions

Figure 1:
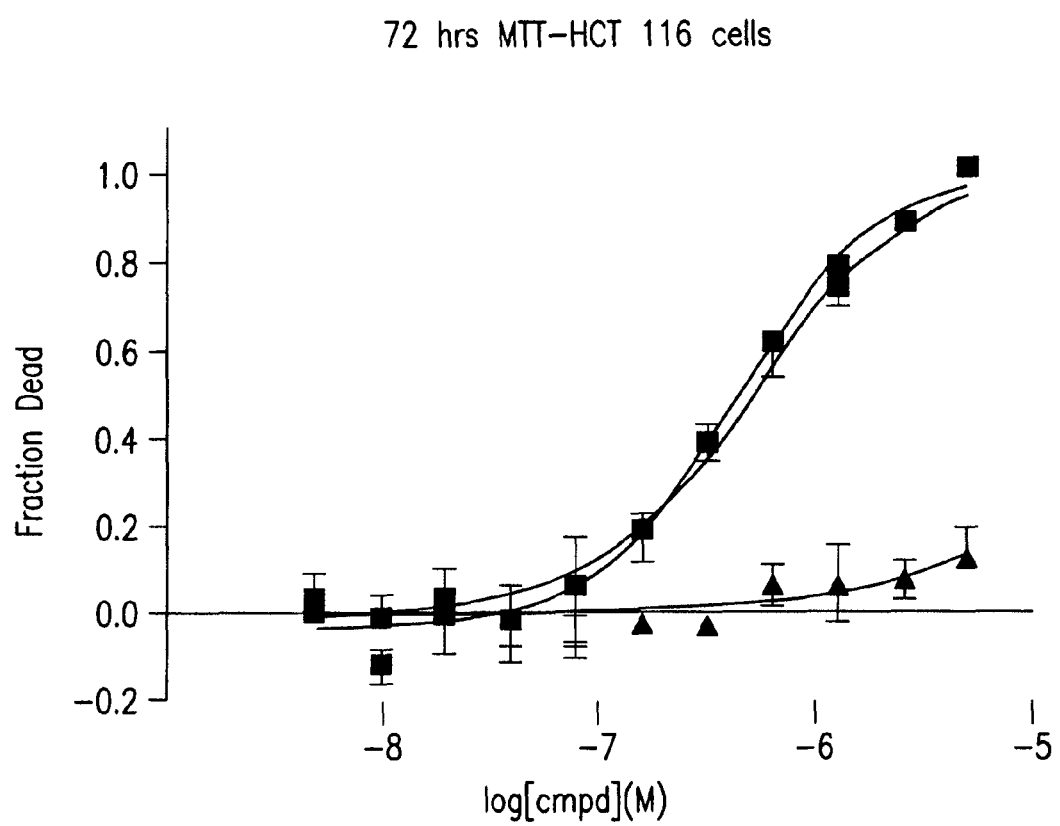

Unless defined otherwise, all technical and scientific terms used herein have the same meaning as is commonly understood by one of ordinary skill in the art. All patents, applications, published applications and other publications noted herein are incorporated by reference in their entirety. In the event that there are a plurality of definitions for a term herein, those in this section prevail unless stated otherwise.

As used herein, "SNS-595" refers to (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid. The compound is also known as AG-7352. The chemical structure of the compound is provided herein. Unless otherwise designated, SNS-595 or (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid refers to the enantiomerically pure form of the compound.

As used herein, enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid is substantially free from (−)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (i.e., in enantiomeric excess). In other words, the "(+)" form of 1,4-dihydro-7-[(3S,4S)-3-methoxy-4-(methylamino)-1-pyrrolidinyl]-4-oxo-1-(2-thiazolyl)-1,8-naphthyridine-3-carboxylic acid is substantially free from the "(−)" form of the compound and is, thus, in enantiomeric excess of the "(−)" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight or more than 97% by weight of the enantiomer.

As used herein "N-desmethyl-SNS-595" or "N-desmethyl (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid" refers to (+)-1,4-dihydro-7-[(3S,4S)-3-methoxy-4-amino-1-pyrrolidinyl]-4-oxo-1-(2-thiazolyl)-1,8-naphthyridine-3-carboxylic acid. The chemical structure for the compound is provided elsewhere herein.

As used herein "O-desmethyl-SNS-595" or "O-desmethyl (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid" refers (+)-1,4-dihydro-7-[(3S,4S)-3-hydroxy-4-methylamino-1-pyrrolidinyl]-4-oxo-1-(2-thiazolyl)-1,8-naphthyridine-3-carboxylic acid. The chemical structure for the compound is provided elsewhere herein.

As used herein, unless specified otherwise, "compound" or "compound provided herein" refers to N-desmethyl(+)-1,4-dihydro-7-[(3S,4S)-3-hydroxy-4-methylamino-1-pyrrolidinyl]-4-oxo-1-(2-thiazolyl)-1,8-naphthyridine-3-carboxylic acid, O-desmethyl(+)-1,4-dihydro-7-[(3S,4S)-3-hydroxy-4-methylamino-1-pyrrolidinyl]-4-oxo-1-(2-thiazolyl)-1,8-naphthyridine-3-carboxylic acid or a glucuronide of (+)-1,4-dihydro-7-[(3S,4S)-3-hydroxy-4-methylamino-1-pyrrolidinyl]-4-oxo-1-(2-thiazolyl)-1,8-naphthyridine-3-carboxylic acid provided herein.

As used herein and unless otherwise indicated, the terms "treat," "treating" and "treatment" refer to alleviating or reducing the severity of a disease or a symptom associated with the disease or condition being treated.

The term "prevention" includes the inhibition of a disease or disorder or a symptom of the particular disease or disorder. In some embodiments, patients with familial history of cancer are candidates for preventive regimens. Generally, the term "preventing" refers to administration of the drug prior to the onset of symptoms, particularly to patients at risk of cancer.

As used herein and unless otherwise indicated, the term "managing" encompasses preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein "subject" is an animal, typically a mammal, including human, such as a patient.

As used herein, the term "cancer" includes, but is not limited to, solid tumors and blood born tumors. In certain embodiment, cancer can be cancer of skin tissues, organs, blood, and vessels, including, but not limited to, cancers of the bladder, bone or blood, brain, breast, cervix, chest, colon, endometrium, esophagus, eye, head, kidney, liver, lung, mouth, neck, ovaries, pancreas, prostate, rectum, stomach, testis, throat and uterus. In certain embodiment, the cancer is hematologic malignancy, such as leukemias, lymphomas (Non-Hodgkin's Lymphoma), Hodgkin's disease (also called Hodgkin's Lymphoma) and myeloma. In certain embodiments, the leukemia is chronic lymphocytic leukemia, chronic myeloid leukemia, acute lymphocytic leukemia, acute myelogenous leukemia and acute myeloblastic leukemia. In certain embodiments, the cancer comprises solid tumor. In certain embodiments, the cancer can be relapsed, refractory or resistant to conventional therapy. In certain embodiments, the cancer can be metastatic.

The term "relapsed" refers to a return of cancer cells or symptoms in patients who have had a previous remission of cancer after therapy.

The terms "refractory" or "resistant" refer to patients that, even after treatment or intensive treatment, have residual cancer cells in their body.

As used herein, the $IC_{50}$ refers to an amount, concentration or dosage of a particular test compound that achieves a 50% inhibition of a maximal response in an assay that measures such response.

As used herein, and unless otherwise specified, the terms "therapeutically effective amount" and "effective amount" of a compound refer to an amount sufficient to provide a therapeutic benefit in the treatment, prevention and/or management of a disease, to delay or minimize one or more symptoms associated with the disease or disorder to be treated. The terms "therapeutically effective amount" and "effective amount" can encompass an amount that improves overall therapy, reduces or avoids symptoms or causes of disease or disorder or enhances the therapeutic efficacy of another therapeutic agent.

As used herein and unless otherwise indicated, the term "pharmaceutically acceptable salt" includes, but is not limited to, salts of acidic or basic groups that can be present in the compounds provided herein. Under certain acidic conditions, the compound can form a wide variety of salts with various inorganic and organic acids. The acids that can be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide and pamoate. Under certain basic conditions, the compound can form base salts with various pharmacologically acceptable cations. Non-limiting examples of such salts include alkali metal or alkaline earth metal salts and, particularly, calcium, magnesium, sodium, lithium, zinc, potassium and iron salts.

As used herein and unless otherwise indicated, the term "hydrate" means a solid or semi-solid comprising a compound provided herein or a salt or molecular complex thereof, that further comprises a stoichiometric or non-stoichiometric amount of water.

As used herein and unless otherwise indicated, the term "solvate" means a solid or semi-solid comprising a compound provided herein or a salt or molecular complex thereof, that further comprises a stoichiometric or non-stoichiometric amount of one or more types of solvent. The term "solvate" includes hydrates (e.g., hemihydrate, monohydrate, sesquihydrate, dihydrate, trihydrate, tetrahydrate and the like).

The terms "co-administration" and "in combination with" include the administration of two therapeutic agents (for example, SNS-595 or a composition provided herein and another anti-cancer agent or second agent) either simultaneously, concurrently or sequentially with no specific time limits. In one embodiment, both agents are present in the cell or in the patient's body at the same time or exert their biological or therapeutic effect at the same time. In one embodiment, the two therapeutic agents are in the same composition or unit dosage form. In another embodiment, the two therapeutic agents are in separate compositions or unit dosage forms.

The term "the supportive care agent" refers to any substance that treats, prevents, manages, reduces or avoids an adverse or unwanted effect from SNS-595 treatment.

6.2 Compounds and Compositions

SNS-595 is enantiomerically pure (+)-1,4-dihydro-7-[(3S, 4S)-3-methoxy-4-(methylamino)-1-pyrrolidinyl]-4-oxo-1-(2-thiazolyl)-1,8-naphthyridine-3-carboxylic acid, which is also known as AG-7352 or SP-9595. SNS-595 has the following chemical structure:

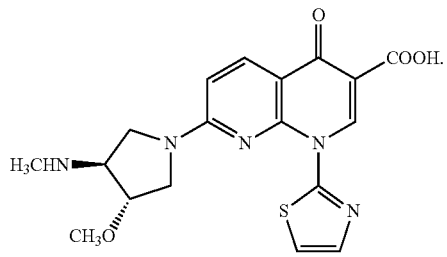

In one embodiment, provided herein is a hydrate comprising SNS-595. In certain embodiment, the hydrate exhibits an X-ray powder diffraction pattern comprising a peak at approximately 8.2 degrees 2θ. In another embodiment, the hydrate exhibits an X-ray powder diffraction pattern further comprising peaks at approximately 6.9, 11.1 and 18.8 degrees 2θ. In a further embodiment, the hydrate exhibits an X-ray powder diffraction pattern further comprising peaks at approximately 16.4, 17.5, 20.8 and 24.9 degrees 2θ.

In one embodiment, the hydrate exhibits a differential scanning calorimetry thermogram comprising an endothermic event with an onset temperature of approximately 126.5° C. when heated from approximately 25° C. to approximately 350° C. at approximately 10° C./min. In another embodiment, the hydrate exhibits a differential scanning calorimetry thermogram further comprising an endothermic event with an onset temperature of approximately 273.3° C. In a further embodiment, the hydrate exhibits a thermogravimetric analysis thermogram comprising a weight loss of approximately 4.4% when heated from approximately 25° C. to approximately 200° C. at approximately 10° C./min.

In certain embodiments, the hydrate comprises between approximately 0.8 and 1.2 molar equivalents of water per mole of SNS-595. In another embodiment, the hydrate comprises between approximately 0.9 to 1.1 molar equivalents of water per mole of SNS-595. In another embodiment, the hydrate comprises between approximately 0.95 to 1.05 molar equivalents of water per mole of SNS-595. In another embodiment, the hydrate comprises between approximately 0.98 to 1.02 molar equivalents of water per mole of SNS-595.

In one embodiment, provided herein are methods of treatment, prevention or amelioration of one or more cancers comprising administering N-desmethyl-SNS-595 or a pharmaceutically acceptable salt, solvate or hydrate thereof in the compositions and dosages described herein. N-desmethyl SNS-595 has the following chemical structure:

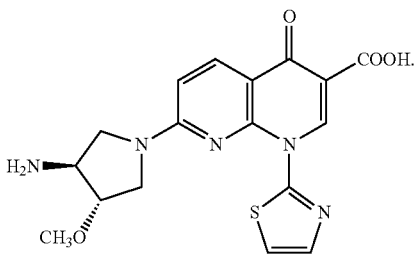

In one embodiment, provided herein is a compound selected from O-desmethyl-SNS-595 and a glucuronide of SNS-595 and pharmaceutically acceptable derivatives, such as salts, solvates or hydrates of the compound. In one embodiment, provided herein is O-desmethyl-SNS-595 or a pharmaceutically acceptable salt, solvate or hydrate thereof and methods of use thereof for treatment, prevention or amelioration of one or more cancers. O-desmethyl SNS-595 has the following chemical structure:

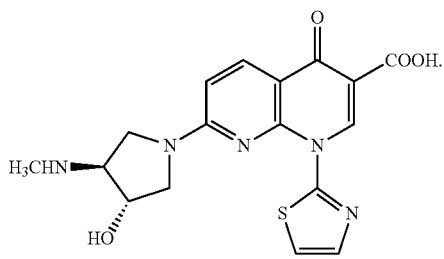

In one embodiment, provided herein is a glucuronide of SNS-595 or a pharmaceutically acceptable salt, solvate or hydrate thereof and methods of use thereof for treatment, prevention or amelioration of one or more cancers. The glucuronide of SNS-595 has the following chemical structure:

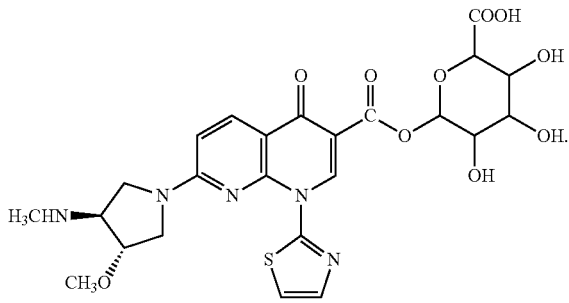

In one embodiment, provided herein is a composition comprising SNS-595 and N-desmethyl-SNS-595. In certain embodiments, the composition provided herein comprises at least 97% SNS-595 by weight of the active component. In one embodiment, the composition comprises at least 98%, at least 98.3%, at least 98.5%, at least 98.7%, at least 98.9%, at least 99%, at least 99.1%, at least 99.2%, at least 99.3%, at least 99.4%, at least 99.5%, at least 99.6%, at least 99.7%, at least 99.8%, at least 99.9%, at least 99.95% or at least 99.99% SNS-595 by weight of the active component. In certain embodiments, the percentages of SNS-595 and N-desmethyl-SNS-595 are based upon total weight of the two components.

In certain embodiments, provided herein is a composition comprising SNS-595 and from about 0.01% up to about 3% by weight of N-desmethyl-SNS-595. In one embodiment, the composition comprises from about 0.1% up to about 2.5%, about 0.2% up to about 2.3%, about 0.3% up to about 2%, about 0.4% up to about 2%, about 0.5% up to about 2%, about 0.6% up to about 2%, about 0.7% up to about 2% or about 0.8% up to about 2% by weight of N-desmethyl-SNS-595. In another embodiment, the composition comprises from about 0.3% up to about 1.8%, about 0.4% up to about 1.5% or about 0.6% up to about 1.5% of N-desmethyl-SNS-595. In other embodiments, the composition comprises about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9% or 2% of N-desmethyl-SNS-595 based upon total weight of SNS-595 and N-desmethyl-SNS-595.

In certain embodiments, the composition comprises N-desmethyl-SNS-595 and from about 99.99% to about 97% of SNS-595 by weight. In one embodiment, the composition comprises from about 99.95% to about 97.5%, about 99.9% to about 98%, about 99.7% to about 98.5% or about 99.5% to about 99% of SNS-595 by weight. In another embodiment, the composition comprises from about 99.7% to about 98.2% of SNS-595 by weight. In other embodiments, the composition comprises about 99.9% 99.8%, 99.7%, 99.6%, 99.5%, 99.4%, 99.3%, 99.2%, 99.1%, 99%, 98.9%, 98.8%, 98.7%, 98.6%, 98.5%, 98.4%, 98.3%, 98.2%, 98.1% or 98% of SNS-595 by weight based upon total weight of SNS-595 and N-desmethyl-SNS-595.

In certain embodiments, provided herein is a composition that comprises from about 99.99% to about 97% of SNS-595 and from about 0.01% up to about 3% by weight of N-desmethyl-SNS-595, wherein each of the percentage is based upon total weight of the two components. In another embodiment, the composition comprises from about 99.95% to about 98% of SNS-595 and from about 0.05% up to about 2% by weight of N-desmethyl-SNS-595. In one embodiment, the composition comprises from about 99.5% to about 98% of SNS-595 and from about 0.5% up to about 2% by weight of N-desmethyl-SNS-595. In other embodiments, the composition comprises about 99.9% SNS-595 and about 0.1% N-desmethyl-SNS-595, about 99.8% SNS-595 and about 0.2% N-desmethyl-SNS-595, about 99.7% SNS-595 and about 0.3% N-desmethyl-SNS-595, about 99.6% SNS-595 and about 0.4% N-desmethyl-SNS-595, 99.5% SNS-595 and about 0.5% N-desmethyl-SNS-595, about 99.4% SNS-595 and about 0.6% N-desmethyl-SNS-595, about 99.3% SNS-595 and about 0.7% N-desmethyl-SNS-595, about 99.2% SNS-595 and about 0.8% N-desmethyl-SNS-595, about 99.1% SNS-595 and about 0.9% N-desmethyl-SNS-595, about 99% SNS-595 and about 1% N-desmethyl-SNS-595, about 98.9% SNS-595 and about 1.1% N-desmethyl-SNS-595, about 98.8% SNS-595 and about 1.2% N-desmethyl-SNS-595, about 98.7% SNS-595 and about 1.3% N-desmethyl-SNS-595, about 98.6% SNS-595 and about 1.4% N-desmethyl-SNS-595, about 98.5% SNS-595 and about 1.5% N-desmethyl-SNS-595, about 98.4% SNS-595 and about 1.6% N-desmethyl-SNS-595, about 98.3% SNS-595 and about 1.7% N-desmethyl-SNS-595, about 98.2% SNS-595 and about 1.8% N-desmethyl-SNS-595, about 98.1% SNS-595 and about 1.9% N-desmethyl-SNS-595, or about 98% SNS-595 and about 2% N-desmethyl-SNS-595 by weight. Each of the above is by weight of the active component.

In certain embodiments, provided herein is a composition comprising about 97% to about 99.99% by weight of a hydrate of SNS-595 and from about 0.01% up to about 3% by weight of an N-desmethyl-SNS-595, wherein each of the percentages is based upon total weight of the two components. In one embodiment, the composition comprises about 0.8% by weight N-desmethyl-SNS-595. In one embodiment, the composition comprises about 1.5% by weight N-desmethyl-SNS-595. In one embodiment, the composition comprises about 98.5% by weight of the hydrate of SNS-595. In one embodiment, the composition comprises about 99.2% by weight of the hydrate of SNS-595.

In certain embodiments, provided herein are methods for assaying the amount of N-desmethyl-SNS-595 in a composition or a biological sample. In certain embodiments, the composition comprises from about 99.99% to about 97% of SNS-595 and from about 0.01% up to about 3% by weight of N-desmethyl-SNS-595. Such methods can be accomplished by techniques known to one of skill in the art and described herein, such as HPLC assays.

Also provided are pharmaceutical compositions comprising the compounds and compositions disclosed herein along with a pharmaceutically acceptable carrier, excipient or adjuvant. In one embodiment, the pharmaceutical composition comprises a composition comprising SNS-595 and N-desmethyl-SNS-595. In another embodiment, the pharmaceutical composition comprises a compound selected from N-desmethyl-SNS-595, O-desmethyl-SNS-595, glucuronide of SNS-595 and pharmaceutically acceptable salt thereof. In one embodiment, the pharmaceutical composition comprises a hydrate of SNS-595, N-desmethyl-SNS-595 and a pharmaceutically acceptable carrier, excipient or adjuvant.

5.3 Methods of Preparation

The compositions provided herein can be prepared using techniques described herein and techniques known to one of skill in the art, for example, Example C-1 of U.S. Pat. No. 5,817,669, titled "Compounds, processes for the preparation thereof and anti-tumor agents," issued Oct. 6, 1998, and in Japanese Patent Application No. Hei 10-173986, to Chikugi et al., which are incorporated herein by reference in their entirety. Certain exemplary pharmaceutical compositions comprising SNS-595 and methods of using the same are described in U.S. Patent Application Pub. Nos. 2005-0203120; 2005-0215583 and 2006-0025437, which are incorporated herein by reference in their entirety.

In an exemplary method for preparation, compositions provided herein are prepared from 2,6-dichloronicotinic acid and either 2-pyrroline or 1,4-dichloro-2-butene as illustrated in the following scheme (Tsuzuki et al., *J. Med. Chem.*, 47:2097-2106, 2004 and Tomita et al., *J. Med. Chem.*, 45: 5564-5575, 2002):

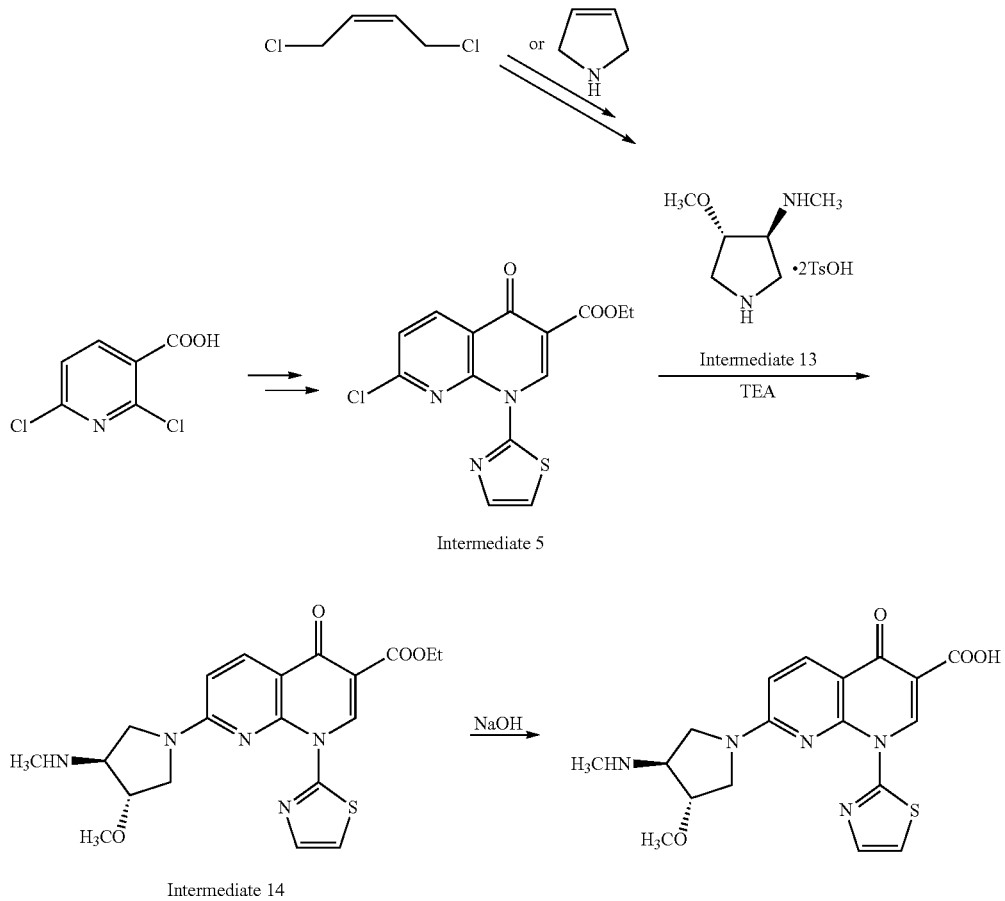

Figure 2:
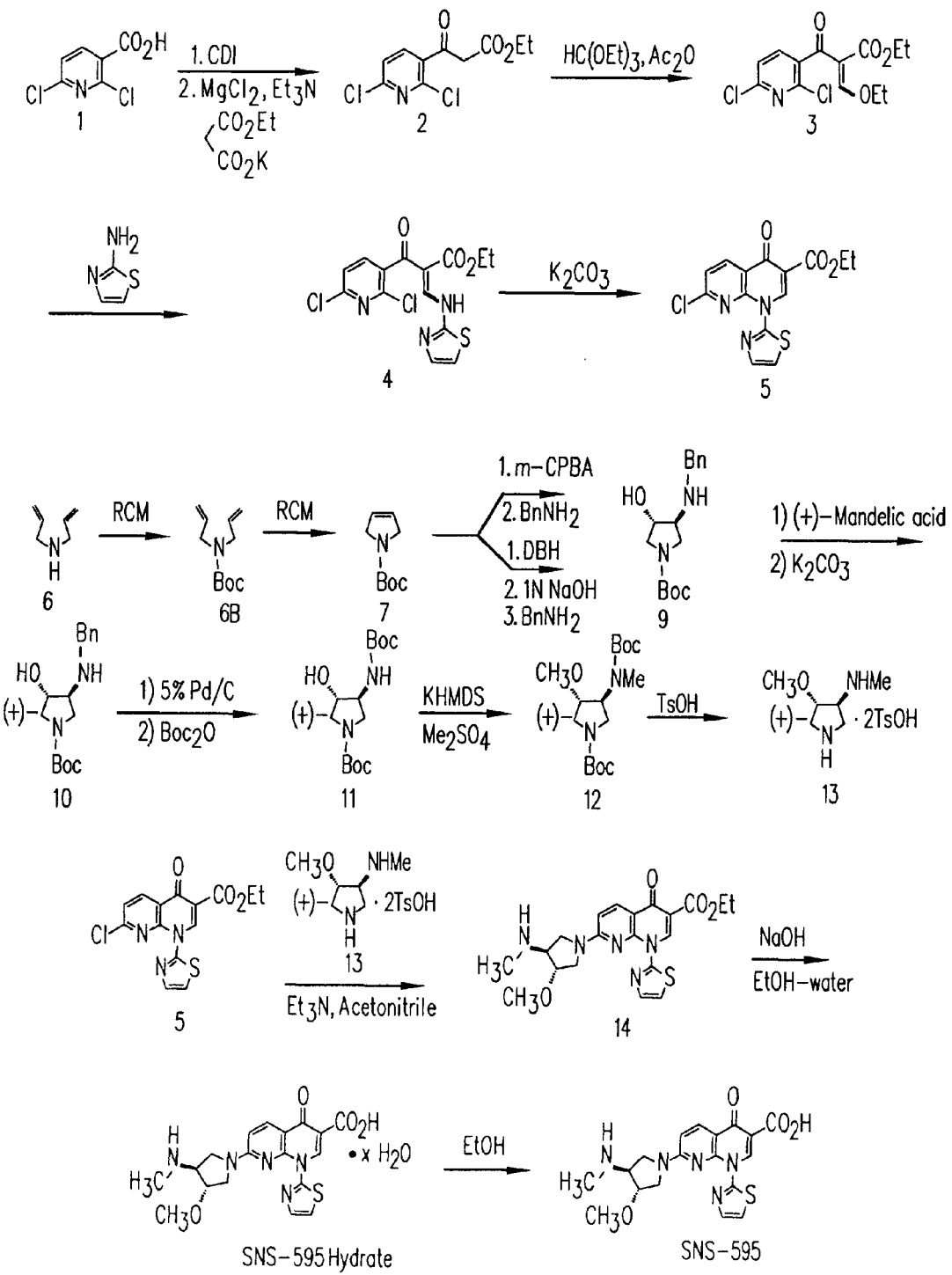

An exemplary synthetic process is described in the Examples section and illustrated in FIG. 2.

5.4 Dosages

In certain representative embodiments, the method of treating, preventing or managing cancers provided herein comprises administering to a patient on the basis of body surface area, a dose of about 1 mg/m$^2$-150 mg/m$^2$ or about 1 mg/m$^2$-75 mg/m$^2$ of a compound or composition provided herein. In another embodiment, the method of comprises administering a dose of about 1 mg/m$^2$-60 mg/m$^2$ of the compound or composition. In another embodiment, the method of comprises administering a dose of about 10 mg/m$^2$-60 mg/m$^2$ of the compound or composition. In another embodiment, the method comprises administering a dose of about 1 mg/m$^2$-50 mg/m$^2$ of the compound or composition. In another embodiment, the method comprises administering a dose of about 1 mg/m$^2$-48 mg/m$^2$ of the compound or composition. In another embodiment, the method of comprises administering a dose of about 10 mg/m$^2$-48 mg/m$^2$ of the compound or composition. In another embodiment, the method comprises administering a dose of about 1 mg/m$^2$-24 mg/m$^2$ of the compound or composition. In another embodiment, the method comprises administering a dose of about 3 mg/m$^2$-27 mg/m$^2$ of the compound or composition provided herein on the basis of body surface area.

The weight of the compound or composition in an administered dose is based on total weight of the active compound or composition, respectively, e.g., total weight of SNS-595 and N-desmethyl SNS-595 or total weight of N-desmethyl-SNS-595.

Body surface area calculations can be calculated for example, with the Mosteller formula wherein:

$$BSA(m^2)=\text{square root of}[(\text{height}(cm)\times\text{weight}(kg))/3600].$$

In another embodiment, the dose is about 10 mg/m$^2$-60 mg/m$^2$ or about 10 mg/m$^2$-48 mg/m$^2$ of the compound or composition on the basis of body surface area. In another embodiment, the dose is about 3 mg/m$^2$-24 mg/m$^2$ of the compound or composition on the basis of body surface area. In another embodiment, the dose is about 3 mg/m$^2$-18 mg/m$^2$ on the basis of body surface area. In another embodiment, the dose is about 3 mg/m$^2$-15 mg/m$^2$ of the compound or composition. In another embodiment, the dose is about 1 mg/m$^2$, 2 mg/m$^2$, 3 mg/m$^2$, 4 mg/m$^2$, 5 mg/m$^2$, 6 mg/m$^2$, 7 mg/m$^2$, 8 mg/m$^2$, 9 mg/m$^2$, 10 mg/m$^2$, 11 mg/m$^2$, 12 mg/m$^2$, 13 mg/m$^2$, 14 mg/m$^2$, 15 mg/m$^2$, 16 mg/m$^2$, 17 mg/m$^2$, 18 mg/m$^2$, 19 mg/m$^2$, 20 mg/m$^2$, 21 mg/m$^2$, 22 mg/m$^2$, 23 mg/m$^2$, 24 mg/m$^2$, 25 mg/m$^2$, 26 mg/m$^2$, 27 mg/m$^2$, 28 mg/m$^2$, 30 mg/m$^2$, 45 mg/m$^2$, 48 mg/m$^2$, 60 mg/m$^2$ or 75 mg/m$^2$ of the compound or composition on the basis of body surface area. In another embodiment, the dose is about 40 mg/m$^2$, 41 mg/m$^2$, 42 mg/m$^2$, 43 mg/m$^2$, 44 mg/m$^2$, 45 mg/m$^2$, 46 mg/m$^2$, 47 mg/m$^2$, 48 mg/m$^2$, 49 mg/m$^2$, 50 mg/m$^2$, 51 mg/m$^2$, 52 mg/m$^2$, 53 mg/m$^2$, 54 mg/m$^2$, 55 mg/m$^2$, 56 mg/m$^2$, 57 mg/m$^2$, 58 mg/m$^2$, 59 mg/m$^2$, 60 mg/m$^2$, 62 mg/m$^2$, 65 mg/m$^2$, 68 mg/m$^2$, 70 mg/m$^2$, 72 mg/m$^2$, 75 mg/m$^2$, 80 mg/m$^2$, 84 mg/m$^2$, 85 mg/m$^2$ or 90 mg/m$^2$ of the compound or composition on the basis of body surface area. In another embodiment, the dose is about 3 mg/m$^2$, 12 mg/m$^2$, 15 mg/m$^2$, 18 mg/m$^2$, 48 mg/m$^2$ or 60 mg/m$^2$ of the compound or composition. In another embodiment, the dose is about 15 mg/m$^2$ of the compound or composition provided herein on the basis of body surface area.

The administered dose of the compound or composition provided herein can be expressed in units other than as mg/m$^2$. For example, doses can be expressed as mg/kg. One of ordinary skill in the art would readily know how to convert doses from mg/m$^2$ to mg/kg to given either the height or weight of a subject or both (see, www.fda.gov/cder/cancer/animalframe.htm). For example, a dose of 1 mg/m$^2$-30 mg/m$^2$ for a 65 kg human is approximately equal to 0.026 mg/kg-0.79 mg/kg. In another example, a dose of 3 mg/m$^2$ for a 65 kg human is approximately equal to 0.078 mg/kg.

In certain embodiments, the administered dose of the compound or composition provided herein can be delivered as a single dose (e.g. a single bolus IV injection) or over a 24-hour period (e.g., continuous infusion over time or divided bolus doses over time) and is repeated until the patient experiences stable disease or regression or until the patient experiences disease progression or unacceptable toxicity. Stable disease or lack thereof is determined by methods known in the art, such as evaluation of patient symptoms, physical examination and other commonly accepted evaluation modalities.

The amount of the pharmaceutical composition administered according to the methods provided herein will depend on various factors, such as the mammal being treated, the severity of the disorder or symptom of the disorder, the active ingredient present, the manner of administration, the frequency of administration and the judgment of the prescribing physician. The amount can be empirically determined by the physician.

In some embodiments, the frequency of administration is in the range of about a daily dose to about a monthly dose. In certain embodiments, administration is once a day to once every other day or from twice a week, once every week, once every two weeks, once every three weeks or once every four weeks. In one embodiment, the pharmaceutical composition provided herein is administered once a week.

In certain embodiments, the compound or composition provided herein is cyclically administered to a patient. Cycling therapy involves the administration of an the compound or composition for a period of time, followed by a rest for a period of time, and repeating this sequential administration. Cycling therapy can reduce the development of resistance to one or more of the therapies, avoid or reduce the side effects of one of the therapies, and/or improve the efficacy of the treatment.

Consequently, in one embodiment, the compound or composition provided herein is administered once a week in a single or divided doses in a three to six week cycle with a rest period of about 1 to about 30 days. In another embodiment, the compound or composition provided herein is administered once a week in a single or divided doses for one week, two weeks, three weeks, four weeks, five weeks or six weeks with a rest period of 1, 3, 5, 7, 9, 12, 14, 16, 18, 20, 21, 22, 24, 26, 28, 29 or 30 days. In some embodiments, the waiting period is 14 days. In some embodiments, the waiting period is 28 days. The frequency, number and length of dosing cycles can be increased or decreased. Thus, another embodiment encompasses the administration of the compound or composition provided herein for more cycles than are typical when the compound or composition is administered alone.

In one embodiment, the method provided herein comprises: i) administering a dose of about 1 mg/m$^2$-150 mg/m$^2$ of the compound or composition provided herein to a patient; ii) waiting a period of at least one day where the mammal is not administered the compound or composition; and iii) administering another dose of about 1 mg/m$^2$-150 mg/m$^2$ of the compound or composition provided herein to the patient. In one embodiment, steps ii)-iii) are repeated a plurality of times.

In one embodiment, the method provided herein comprises: i) administering a dose of about 1 mg/m$^2$-75 mg/m$^2$ of the compound or composition provided herein to a patient; ii) waiting a period of at least one day where the mammal is not administered the compound or composition; and iii) administering another dose of about 1 mg/m$^2$-75 mg/m$^2$ of the compound or composition provided herein to the patient. In one embodiment, steps ii)-iii) are repeated a plurality of times.

In one embodiment, the method provided herein comprises: i) administering a dose of about 1 mg/m$^2$-75 mg/m$^2$ of the compound or composition provided herein to a patient; ii) waiting a period of at least two days where the mammal is not administered the compound or composition; and iii) administering another dose of about 1 mg/m$^2$-75 mg/m$^2$ of the compound or composition provided herein to the patient. In one embodiment, steps ii)-iii) are repeated a plurality of times. In yet another embodiment, the method comprises administering a dose of about 1 mg/m$^2$-50 mg/m$^2$, 1 mg/m$^2$-60 mg/m$^2$, 10 mg/m$^2$-60 mg/m$^2$ or about 1 mg/m$^2$-48 mg/m$^2$ of the compound or composition provided herein in steps i) and iii). In yet another embodiment, the method comprises administering a dose of about 15 mg/m$^2$, 48 mg/m$^2$, 50 mg/m$^2$, 60 mg/m$^2$ or 75 mg/m$^2$ of the compound or composition provided herein in steps i) and iii).

In one embodiment, the method provided herein comprises: i) administering a dose of about 1 mg/m$^2$-75 mg/m$^2$ of the compound or composition provided herein to a patient; ii) waiting a period of at least 7 days where the mammal is not administered the compound or composition; and iii) administering another dose of about 1 mg/m$^2$-75 mg/m$^2$ of the compound or composition provided herein to the patient. In one embodiment, steps ii)-iii) are repeated a plurality of times. In yet another embodiment, the method comprises administering a dose of about 1 mg/m$^2$-50 mg/m$^2$ or about 1 mg/m$^2$-48 mg/m$^2$ of the compound or composition provided herein in steps i) and iii). In yet another embodiment, the method comprises administering a dose of about 15 mg/m$^2$, 48 mg/m$^2$, 50 mg/m$^2$, 60 mg/m$^2$ or 75 mg/m$^2$ of the compound or composition provided herein in steps i) and iii).

In one embodiment, the method provided herein comprises: i) administering a dose of about 1 mg/m$^2$-150 mg/m$^2$ of the compound or composition provided herein to a patient; ii) waiting a period of at least 14 days where the mammal is not administered the compound or composition; and iii) administering another dose of about 1 mg/m$^2$-150 mg/m$^2$ of the compound or composition provided herein to the patient. In one embodiment, the method provided herein comprises: i) administering a dose of about 1 mg/m$^2$-75 mg/m$^2$ of the compound or composition provided herein to a patient; ii) waiting a period of at least 14 days where the mammal is not administered the compound or composition; and iii) administering another dose of about 1 mg/m$^2$-75 mg/m$^2$ of the compound or composition provided herein to the patient. In one embodiment, steps ii)-iii) are repeated a plurality of times. In yet another embodiment, the method comprises administering a dose of about 1 mg/m$^2$-50 mg/m$^2$, 1 mg/m$^2$-60 mg/m$^2$, 10 mg/m$^2$-60 mg/m$^2$ or about 1 mg/m$^2$-48 mg/m$^2$ of the compound or composition provided herein in steps i) and iii). In yet another embodiment, the method comprises administering a dose of about 15 mg/m$^2$, 48 mg/m$^2$, 50 mg/m$^2$, 60 mg/m$^2$ or 75 mg/m$^2$ of the compound or composition provided herein in steps i) and iii).

In one embodiment, the method provided herein comprises: i) administering a dose of about 10 mg/m$^2$-60 mg/m$^2$ of the compound or composition provided herein to a patient; ii) waiting a period of at least one day where the mammal is not administered the compound or composition; and iii) administering another dose of about 10 mg/m$^2$-60 mg/m$^2$ of the compound or composition provided herein to the patient. In one embodiment, steps ii)-iii) are repeated a plurality of times.

In one embodiment, the method provided herein comprises: i) administering a dose of about 10 mg/m$^2$-60 mg/m$^2$ of the compound or composition provided herein to a patient; ii) waiting a period of at least 7 days where the mammal is not administered the compound or composition; and iii) administering another dose of about 10 mg/m$^2$-60 mg/m$^2$ of the compound or composition provided herein to the patient. In one embodiment, steps ii)-iii) are repeated a plurality of times.

In one embodiment, the method provided herein comprises: i) administering a dose of about 10 mg/m$^2$-60 mg/m$^2$ of the compound or composition provided herein to a patient; ii) waiting a period of at least 14 days where the mammal is not administered the compound or composition; and iii) administering another dose of about 10 mg/m$^2$-60 mg/m$^2$ of the compound or composition provided herein to the patient. In one embodiment, steps ii)-iii) are repeated a plurality of times.

In one embodiment, the method provided herein comprises: i) administering a dose of about 1 mg/m$^2$-48 mg/m$^2$ of the compound or composition provided herein to a patient; ii) waiting a period of at least one day where the mammal is not administered compound or composition; and iii) administering another dose of about 1 mg/m$^2$-48 mg/m$^2$ of the compound or composition to the patient. In one embodiment, steps ii)-iii) are repeated a plurality of times.

In one embodiment, the method provided herein comprises: i) administering a dose of about 1 mg/m$^2$-24 mg/m$^2$ of the compound or composition provided herein to a patient; ii) waiting a period of at least one day where the mammal is not administered the compound or composition; and iii) administering another dose of about 1 mg/m$^2$-24 mg/m$^2$ of the compound or composition to the patient. In one embodiment, steps ii)-iii) are repeated a plurality of times.

In another embodiment, the method comprises administering a dose of about 3 mg/m$^2$-24 mg/m$^2$ of the compound or composition in steps i) and iii). In yet another embodiment, the method comprises administering a dose of about 15 mg/m$^2$ in steps i) and iii). In yet another embodiment, the method comprises administering a dose of about 1 mg/m$^2$-40 mg/m$^2$, about 1.5 mg/m$^2$-30 mg/m$^2$, about 2 mg/m$^2$-25 mg/m$^2$ or about 3 mg/m$^2$-24 mg/m$^2$ of the compound or composition provided herein in steps i) and iii).

In one embodiment, the method provided herein comprises: i) administering a dose of about 1 mg/m$^2$-60 mg/m$^2$ or about 10 mg/m$^2$-60 mg/m$^2$ of the compound or composition provided herein to a patient; ii) waiting a period of at least one day where the mammal is not administered the compound or composition; and iii) administering another dose of about 1 mg/m$^2$-60 mg/m$^2$ or about 10 mg/m$^2$-60 mg/m$^2$ of the compound or composition provided herein to the patient. In one embodiment, steps ii)-iii) are repeated a plurality of times. In one embodiment, the waiting period is 6 days. In one embodiment, steps ii)-iii) are repeated a plurality of times. In one embodiment, the waiting period is 7 days. In one embodiment, steps ii)-iii) are repeated a plurality of times. In one embodiment, the waiting period is 14 days. In one embodiment, the waiting period is 18 days. In one embodiment, the waiting period is 21 days.

In one embodiment, the method provided herein comprises i) administering a dose of about 1 mg/m$^2$-75 mg/m$^2$ of the compound or composition provided herein to a patient once every week for three weeks and ii) waiting for a period of 14 days. In one embodiment, the method provided herein comprises i) administering a dose of about 1 mg/m$^2$-60 mg/m$^2$ or about 10 mg/m$^2$-60 mg/m$^2$ of the compound or composition provided herein to a patient once every week for three weeks and ii) waiting for a period of 14 days. In one embodiment, steps i)-ii) are repeated a plurality of times.

In one embodiment, the method provided herein comprises i) administering a dose of about 10 mg/m$^2$-48 mg/m$^2$ of the compound or composition provided herein to a patient once every week for three weeks and ii) waiting for a period of 14 days. In one embodiment, steps ii)-ii) are repeated a plurality of times.

In one embodiment, the method provided herein comprises i) administering a dose of about 15 mg/m$^2$ of the compound or composition provided herein to a patient once every week for three weeks, ii) waiting for a period of 7 days and iii) administering another dose of about 15 mg/m$^2$ of the compound or composition provided herein to a patient once every week for three weeks. In one embodiment, steps ii)-iii) are repeated a plurality of times.

In one embodiment, the method provided herein comprises i) administering a dose of about 15 mg/m$^2$ of the compound or composition provided herein to a patient once every week for three weeks, ii) waiting for a period of 14 days and iii) administering another dose of about 15 mg/m$^2$ of the compound or composition provided herein to a patient once every week for three weeks. In one embodiment, steps ii)-iii) are repeated a plurality of times.

In one embodiment, the method provided herein comprises administering a dose of about 60 mg/m$^2$ of the compound or composition provided herein to a patient once every three weeks. In one embodiment, the method provided herein comprises administering a dose of about 48 mg/m$^2$ of the compound or composition provided herein to a patient once every three weeks. In one embodiment, the method provided herein is for treatment of solid tumors. In one embodiment, the method is for treatment of leiomyosarcoma, melanoma, mesothelioma, mesothelioma, nasopharyngeal, renal cell cancer, salivary gland cancer, lung cancer, adenocarcinoma (unknown origin), ovarian cancer, colon cancer, neuroendocrine, or müllerian tumor.

In another embodiment, the method provided herein comprises: i) administering a dose of about 3 mg/m$^2$-24 mg/m$^2$ of the compound or composition to a mammal once a week for 3 weeks (e.g. dosing in days 1, 8 and 15); ii) waiting a period of at least 28 days where the mammal is not administered the compound or composition; and iii) administering another dose of about 3 mg/m$^2$-24 mg/m$^2$ of the compound or composition to the mammal once a week for 3 weeks. In one embodiment, steps ii)-iii) are repeated a plurality of times.

In another embodiment, the method provided herein comprises: i) administering a dose of about 10 mg/m$^2$-60 mg/m$^2$ of the compound or composition to a mammal once a week for 3 weeks (e.g. dosing in days 1, 8 and 15); ii) waiting a period of at least 28 days where the mammal is not administered the compound or composition; and iii) administering another dose of about 10 mg/m$^2$-60 mg/m$^2$ of the compound or composition to the mammal once a week for 3 weeks. In one embodiment, steps ii)-iii) are repeated a plurality of times.

In another embodiment, the method provided herein comprises: i) administering a dose of about 3 mg/m$^2$-24 mg/m$^2$ of the compound or composition to a mammal once a week for 3 weeks (e.g. dosing in days 1, 8 and 15); ii) waiting a period of 28 days where the mammal is not administered the compound or composition; and iii) administering another dose of about 3 mg/m$^2$-24 mg/m$^2$ of the compound or composition to the mammal once a week for 3 weeks. In one embodiment, steps ii)-iii) are repeated a plurality of times.

In another embodiment, the method provided herein comprises: i) administering a dose of about 10 mg/m$^2$-60 mg/m$^2$ of the compound or composition to a mammal once a week for 3 weeks (e.g. dosing in days 1, 8 and 15); ii) waiting a period of 28 days where the mammal is not administered the compound or composition; and iii) administering another dose of about 10 mg/m$^2$-60 mg/m$^2$ of the compound or composition to the mammal once a week for 3 weeks. In one embodiment, steps ii)-iii) are repeated a plurality of times.

In another embodiment, the method provided herein comprises: i) administering a dose of about 1 mg/m$^2$-75 mg/m$^2$ of the compound or composition to a mammal twice a week for 2 weeks (dosing in days 1, 4, 8 and 11); ii) waiting a period of at least 7 days where the mammal is not administered the compound or composition; and iii) administering another dose of about 1 mg/m$^2$-75 mg/m$^2$ of the compound or composition to the mammal twice a week for 2 weeks (dosing in days 1, 4, 8 and 11). In one embodiment, steps ii)-iii) are repeated a plurality of times. In yet another embodiment, the method comprises administering a dose of about 1 mg/m$^2$-50 mg/m$^2$, 1 mg/m$^2$-60 mg/m$^2$, 10 mg/m$^2$-60 mg/m$^2$ or about 1 mg/m$^2$-48 mg/m$^2$ of the compound or composition provided herein in steps i) and iii). In yet another embodiment, the method comprises administering a dose of about 15 mg/m$^2$, 48 mg/m$^2$, 50 mg/m$^2$, 60 mg/m$^2$ or 75 mg/m$^2$ of the compound or composition provided herein in steps i) and iii).

In another embodiment, the method provided herein comprises: i) administering a dose of about 1 mg/m$^2$-75 mg/m$^2$ of the compound or composition to a mammal twice a week for 2 weeks (dosing in days 1, 4, 8 and 11); ii) waiting a period of at least 14 days where the mammal is not administered the compound or composition; and iii) administering another dose of about 1 mg/m$^2$-75 mg/m$^2$ of the compound or composition to the mammal twice a week for 2 weeks (dosing in days 1, 4, 8 and 11). In one embodiment, steps ii)-iii) are repeated a plurality of times. In yet another embodiment, the method comprises administering a dose of about 1 mg/m$^2$-50 mg/m$^2$, 1 mg/m$^2$-60 mg/m$^2$, 10 mg/m$^2$-60 mg/m$^2$ or about 1 mg/m$^2$-48 mg/m$^2$ of the compound or composition provided herein in steps i) and iii). In yet another embodiment, the method comprises administering a dose of about 15 mg/m$^2$, 48 mg/m$^2$, 50 mg/m$^2$, 60 mg/m$^2$ or 75 mg/m$^2$ of the compound or composition provided herein in steps i) and iii).

In another embodiment, the method provided herein comprises: i) administering a dose of about 3 mg/m$^2$-24 mg/m$^2$ of the compound or composition to a mammal twice a week for 2 weeks (dosing in days 1, 4, 8 and 11); ii) waiting a period of at least 28 days where the mammal is not administered the compound or composition; and iii) administering another dose of about 3 mg/m$^2$-24 mg/m$^2$ of the compound or composition to the mammal twice a week for 2 weeks (dosing in days 1, 4, 8 and 11). In one embodiment, steps ii)-iii) are repeated a plurality of times.

In another embodiment, the method provided herein comprises: i) administering a dose of about 1 mg/m$^2$-75 mg/m$^2$ of the compound or composition to a mammal twice a week for 2 weeks (dosing in days 1, 4, 8 and 11); ii) waiting a period of at least 28 days where the mammal is not administered the compound or composition; and iii) administering another dose of about 1 mg/m$^2$-75 mg/m$^2$ of the compound or composition to the mammal twice a week for 2 weeks (dosing in days 1, 4, 8 and 11). In one embodiment, steps ii)-iii) are repeated a plurality of times.

In another embodiment, the method provided herein comprises: i) administering a dose of about 10 mg/m$^2$-60 mg/m$^2$ of the compound or composition to a mammal twice a week for 2 weeks (dosing in days 1, 4, 8 and 11); ii) waiting a period of at least 28 days where the mammal is not administered the compound or composition; and iii) administering another dose of about 10 mg/m$^2$-60 mg/m$^2$ of the compound or composition to the mammal twice a week for 2 weeks (dosing in days 1, 4, 8 and 11). In one embodiment, steps ii)-iii) are repeated a plurality of times.

In another embodiment, the method provided herein comprises: i) administering a dose of about 3 mg/m$^2$-24 mg/m$^2$ of the compound or composition to a mammal twice a week for 2 weeks (dosing in days 1, 4, 8 and 11); ii) waiting a period of 28 days where the mammal is not administered the compound or composition; and iii) administering another dose of about 3 mg/m$^2$-24 mg/m$^2$ of the compound or composition to the mammal twice a week for 2 weeks (dosing in days 1, 4, 8 and 11). In one embodiment, steps ii)-iii) are repeated a plurality of times.

In another embodiment, the method provided herein comprises: i) administering a dose of about 10 mg/m$^2$-60 mg/m$^2$ of the compound or composition to a mammal twice a week for 2 weeks (dosing in days 1, 4, 8 and 11); ii) waiting a period of 28 days where the mammal is not administered the compound or composition; and iii) administering another dose of about 10 mg/m$^2$-60 mg/m$^2$ of the compound or composition to the mammal twice a week for 2 weeks (dosing in days 1, 4, 8 and 11). In one embodiment, steps ii)-iii) are repeated a plurality of times.

In one embodiment, the method for treatment of solid tumors provided herein comprises i) administering a dose of about 15 mg/m$^2$ of the compound or composition provided herein to a patient once every week for three weeks and ii) waiting for a period of 14 days. In one embodiment, steps ii)-iii) are repeated a plurality of times.

In one embodiment, the method for treatment of solid tumors provided herein comprises i) administering a dose of about 15 mg/m$^2$ of the compound or composition provided herein to a patient once every week for three weeks and ii) waiting for a period of 7 days. In one embodiment, steps ii)-iii) are repeated a plurality of times.

In another embodiment, provided herein is a method for treatment of solid tumors comprising administering a dose of about 48 mg/m$^2$, 60 mg/m$^2$ or 75 mg/m$^2$ of the compound or composition provided herein to a patient once every three weeks.

In another embodiment, provided herein is a method for treatment of leukemia comprising administering a dose of about 40 mg/m$^2$, 50 mg/m$^2$, 60 mg/m$^2$ or 72 mg/m$^2$ of the compound or composition provided herein to a patient once every three weeks.

In another embodiment, provided herein is a method for treatment of leukemia comprising administering a dose of about 40 mg/m$^2$ or 50 mg/m$^2$ of the compound or composition provided herein to a patient once every three weeks.

In one embodiment, leukemia is acute leukemia. In one embodiment, leukemia is relapsed and/or refractory acute leukemia. In one embodiment, leukemia is relapsed acute leukemia. In one embodiment, leukemia is refractory acute leukemia.

In another embodiment, the dosing method comprises administering a dose of the compound or composition twice a week (dosing on days 1, 4, 8 and 11) to a mammal.

In another embodiment, the dosing method comprises administering a once a week dose of the compound or composition to a mammal. In another embodiment, the dosing method comprises administering a dose of the compound or composition to a mammal once every two weeks. In another embodiment, the dosing method comprises administering a dose of the compound or composition to a mammal once every three weeks. In another embodiment, the dosing method comprises administering a dose of the compound or composition to a mammal once every four weeks.

In another embodiment, the dosing method comprises a cycle wherein the cycle comprises administering a dose of the compound or composition to a mammal once a week for three weeks followed by a period of at least 14 days where no compound or composition is administered to the mammal and wherein the cycle is repeated a plurality of times. In another embodiment, the period where no compound or composition is administered is 18 days. In another embodiment, the period where no compound or composition is administered is 21 days. In another embodiment, the period where no compound or composition is administered is 28 days.

In the above methods, if the waiting period were 6 days, then the initial dose of the compound or composition is administered on Day 1 (step i); the waiting period is six days (step ii); and the following dose of the compound or composition is administered on Day 8 (step iii). Other exemplary time periods include 2 days, 3 days, 5 days, 7 days, 10 days, 12 days, 13 days, 14 days, 15 days, 17 days, 20 days, 21 days and 28 days. In one embodiment, the waiting period is until there is sufficient bone marrow recovery. In another embodiment, the waiting period is at least 2 days and steps ii) through iii) are repeated at least three times. In another embodiment, the waiting period is at least 2 days and steps ii) through iii) are repeated at least five times. In another embodiment, the waiting period is at least 3 days and steps ii) through iii) are repeated at least three times. In another embodiment, the waiting period is at least 3 days and steps ii) through iii) are repeated at least five times. In another embodiment, the waiting period is at least 6 days and steps ii) through iii) are repeated at least three times. In another embodiment, the waiting period is at least 6 days and steps ii) through iii) are repeated at least five times. In another embodiment, the waiting period is at least 14 days and steps ii) through iii) are repeated at least three times. In another embodiment, the waiting period is at least 14 days and steps ii) through iii) are repeated at least five times. In another embodiment, the waiting period is at least 20 days and steps ii) through iii) are repeated at least three times. In another embodiment, the waiting period is at least 20 days and steps ii) through iii) are repeated at least five times. In another embodiment, the waiting period is at least 28 days and steps ii) through iii) are repeated at least three times. In another embodiment, the waiting period is at least 28 days and steps ii) through iii) are repeated at least five times.

In another embodiment, the method comprises administering a dose of 1 mg/m$^2$-75 mg/m$^2$ of the compound or composition to a patient once a week wherein the one-week period comprises a treatment cycle and the treatment cycle is repeated at least three times. In another embodiment, the method comprises administering a dose of 1 mg/m$^2$-60 mg/m$^2$ of the compound or composition to a patient once a week wherein the one-week period comprises a treatment cycle and the treatment cycle is repeated at least three times. In another embodiment, the method comprises administering a dose of 1 mg/m$^2$-48 mg/m$^2$ of the compound or composition to a patient once a week wherein the one-week period comprises a treatment cycle and the treatment cycle is repeated at least three times. In another embodiment, the method comprises administering a dose of 1 mg/m$^2$-24 mg/m$^2$ of the compound or composition to a patient once a week wherein the one-week period comprises a treatment cycle and the treatment cycle is repeated at least three times. In another embodiment, the dose is about 2 mg/m$^2$-40 mg/m$^2$ of the compound or composition once a week wherein the one-week period comprises a treatment cycle and the treatment cycle is repeated at least three times. In another embodiment, the dose is about 3 mg/m$^2$-24 mg/m$^2$ of the compound or composition once a week wherein the one-week period comprises a treatment cycle and the treatment cycle is repeated at least three times. In another embodiment, the dose is about 15 mg/m$^2$ of the compound or composition once a week wherein the one-week period comprises a treatment cycle and the treatment cycle is repeated at least three times.

In some embodiments, the method comprises administering a dose of about 10 mg/m$^2$-60 mg/m$^2$ of the compound or composition to a patient once a week (e.g. dosing in days 1, 8 and 15) wherein the one-week period comprises a treatment cycle and the treatment cycle is repeated at least three times followed by a waiting period of at least 28 days. In some embodiments, the method comprises administering a dose of about 10 mg/m$^2$-48 mg/m$^2$ of the compound or composition to a patient once a week (e.g. dosing in days 1, 8 and 15) wherein the one-week period comprises a treatment cycle and the treatment cycle is repeated at least three times followed by a waiting period of at least 28 days. In some embodiments, the method comprises administering a dose of about 10 mg/m$^2$-48 mg/m$^2$ of the compound or composition to a patient twice a week (dosing in days 1, 4, 8, and 11) wherein the one-week period comprises a treatment cycle and the treatment cycle is repeated at least three times followed by a waiting period of at least 28 days. In some embodiments, the method comprises administering a dose of about 10 mg/m$^2$-60 mg/m$^2$ of the compound or composition to a patient once a week (e.g. dosing in days 1, 8 and 15) wherein the one-week period comprises a treatment cycle and the treatment cycle is repeated at least three times followed by a waiting period of 28 days. In some embodiments, the method comprises administering a dose of about 10 mg/m$^2$-48 mg/m$^2$ of the compound or composition to a patient once a week (e.g. dosing in days 1, 8 and 15) wherein the one-week period comprises a treatment cycle and the treatment cycle is repeated at least three times followed by a waiting period of 28 days. In some embodiments, the method comprises administering a dose of about 10 mg/m$^2$-48 mg/m$^2$ of the compound or composition to a patient twice a week (dosing in days 1, 4, 8, and 11) wherein the one-week period comprises a treatment cycle and the treatment cycle is repeated at least three times followed by a waiting period of 28 days. In some embodiments, the method comprises administering a dose of about 3 mg/m$^2$-24 mg/m$^2$ of the compound or composition to a patient once a week (e.g. dosing in days 1, 8 and 15) wherein the one-week period comprises a treatment cycle and the treatment cycle is repeated at least three times followed by a waiting period of at least 28 days. In some embodiments, the method comprises administering a dose of about 3 mg/m$^2$-24 mg/m$^2$ of the compound or composition to a patient twice a week (dosing in days 1, 4, 8, and 11) wherein the one-week period comprises a treatment cycle and the treatment cycle is repeated at least three times followed by a waiting period of at least 28 days. In some embodiments, the method comprises administering a dose of about 3 mg/m$^2$-24 mg/m$^2$ of the compound or composition to a patient once a week (e.g. dosing in days 1, 8 and 15) wherein the one-week period comprises a treatment cycle and the treatment cycle is repeated at least three times followed by a waiting period of 28 days. In some embodiments, the method comprises administering a dose of about 3 mg/m$^2$-24 mg/m$^2$ of the compound or composition to a patient twice a week (dosing in days 1, 4, 8, and 11) wherein the one-week period comprises a treatment cycle and the treatment cycle is repeated at least three times followed by a waiting period of 28 days. All methods and dosages described herein apply to the treatment or prevention of cancer.

In certain embodiments, the methods provided herein comprise monitoring an amount of N-desmethyl-SNS-595 in a subject administered with a pharmaceutical composition comprising SNS-595. The subject can be any subject for which such monitoring might be useful. For example, an exemplary method for detection of N-desmethyl SNS-595 generated in vitro is described in the Examples section. Other methods known to one of skill in the art could be used.

5.5 Second Active Agents

In the methods and pharmaceutical compositions provided herein, the compound or composition provided herein can be used with or combined with other pharmacologically active compounds ("second active agents"). It is believed that certain combinations work synergistically in the treatment of particular types of cancers. The compound or composition provided herein can also work to alleviate adverse effects associated with certain second active agents, and some second active agents can be used to alleviate adverse effects associated with the compound or composition provided herein.

One or more second active ingredients or agents can be used in the methods and pharmaceutical compositions provided herein together with the compound or composition provided herein. Second active agents can be large molecules (e.g., proteins) or small molecules (e.g., synthetic inorganic, organometallic or organic molecules).

Examples of large molecule active agents include, but are not limited to, hematopoietic growth factors, cytokines, and monoclonal and polyclonal antibodies, particularly therapeutic antibodies to cancer antigens. Typical large molecule active agents are biological molecules, such as naturally occurring or artificially made proteins. Proteins that are particularly useful in the methods and compositions provided herein include proteins that stimulate the survival and/or proliferation of hematopoietic precursor cells and immunologically active poetic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; G-CSF (Granulocyte colony-stimulating factor) and GM-CSF (Granulocyte-macrophage colony-stimulating factor); and EPO (Erythropoietin).

Particular proteins that can be used in the methods and compositions include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

Also provided for use in combination with the compounds and compositions provided herein are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with SNS-595 include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), and G250. SNS-595 can also be combined with or used in combination with, anti-TNF-α antibodies.

Large molecule active agents may be administered in the form of anti-cancer vaccines. For example, vaccines that secrete or cause the secretion of, cytokines such as IL-2, G-CSF, and GM-CSF can be used in the methods and pharmaceutical compositions provided. See, e.g., Emens, L. A., et al., *Curr. Opinion Mol. Ther.* 3(1):77-84 (2001).

Second active agents that are small molecules can also be used to alleviate adverse effects associated with the administration of the compound or composition provided herein. However, like some large molecules, many are believed to be capable of providing a synergistic effect when administered with (e.g., before, after or simultaneously) the compound or composition provided herein. Examples of small molecule second active agents include, but are not limited to, anti-cancer agents, antibiotics, immunosuppressive agents, and steroids.

Examples of anti-cancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; vinorelbine; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O$^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, rituximab; oblimersen (Genasense®); remicade; docetaxel; celecoxib; melphalan; dexamethasone (Decadron®); steroids; gemcitabine; cisplatinum; temozolomide; etoposide; cyclophosphamide; temodar; carboplatin; procarbazine; gliadel; tamoxifen; topotecan; methotrexate; Arisa®; taxol; taxotere; fluorouracil; leucovorin; irinotecan; xeloda; CPT-11; interferon alpha; pegylated interferon alpha (e.g., PEG INTRON-A); capecitabine; cisplatin; thiotepa; fludarabine; carboplatin; liposomal daunorubicin; cytarabine; doxetaxol; paclitaxel; vinblastine; IL-2; GM-CSF; dacarbazine; vinorelbine; zoledronic acid; palmitronate; biaxin; busulphan; prednisone; bisphosphonate; arsenic trioxide; vincristine; doxorubicin (Doxil®); paclitaxel; ganciclovir; adriamycin; estramustine sodium phosphate (Emcyt®); sulindac; and etoposide.

In certain embodiments, the second active agent is etoposide; daunomycin; actinomycin D; mitomycin C; cisplatin; carboplatin; premetrexed; methotrexate; Ara-C; 5-Fu; wortmannin; gemcitabin; geldanamycin or a combination thereof.

5.6 Combination Therapy with a Second Active Agent

In certain embodiments, the method provided herein comprises administering a compound or composition provided herein in combination with one or more second active agents, and/or in combination with radiation therapy or surgery. The administration of the compound or composition and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. Recommended routes of administration for the second active agents are known to those of ordinary skill in the art. See, e.g., *Physicians' Desk Reference*, 1755-1760 (56$^{th}$ ed., 2002).

In one embodiment, the second active agent is administered intravenously or subcutaneously and once or twice daily in an amount of from about 1 to about 1,000 mg, from about 5 to about 500 mg, from about 10 to about 375 mg or from about 50 to about 200 mg. In one embodiment, the second active agent is rituximab, oblimersen (Genasense®), GM-CSF, G-CSF, EPO, taxotere, irinotecan, dacarbazine, transretinoic acid, topotecan, pentoxifylline, ciprofloxacin, dexamethasone, vincristine, doxorubicin, COX-2 inhibitor, IL2, IL8, IL18, IFN, Ara-C, vinorelbine or a combination thereof. In certain embodiments, the second active agent is etoposide, daunomycin, actinomycin D, mitomycin C, cisplatin, carboplatin, premetrexed, methotrexate, Ara-C (cytarabine), 5-FU (Fluorouracil), wortmannin, geldanamycin, gemcitabine or a combination thereof.

In another embodiment, provided herein are methods of treating, preventing and/or managing hematologic malignancies, which comprise administering a compound or composition provided herein in conjunction with (e.g., before, during or after) conventional therapy including, but not limited to, surgery, immunotherapy, biological therapy, radiation therapy or other non-drug based therapy presently used to treat, prevent or manage cancer.

In certain embodiments, the second active agent is co-administered with a compound or composition provided herein or administered with 1-50 hours delay. In certain embodiments, a compound or composition provided herein is administered first followed by administration with the second active agent with 1-50 hours delay. In other embodiments, the second active agent is administered first followed by administration of a compound or composition provided herein with 1-50 hours delay. In some embodiment, the delay is 24 hours.

In one embodiment, a compound or composition provided herein can be administered in an amount of from about 1 to about 150 mg/m$^2$, 1 to about 75 mg/m$^2$, 1 to about 60 mg/m$^2$, 1 to about 48 mg/m$^2$, 1 to about 24 mg/m$^2$, 1 to about 50 mg/m$^2$, about 1 to about 40 mg/m$^2$, about 1 to about 30 mg/m$^2$, about 3 to about 30 mg/m$^2$, about 3 to about 24 mg/m$^2$ alone or in combination with a second active agent disclosed herein (see, e.g., section 5.6), prior to, during, or after the use of conventional therapy.

In another embodiment, the method provided herein comprises: a) administering to a patient in need thereof, a dose of about 1 mg/m$^2$-75 mg/m$^2$ of a compound or composition provided herein and b) administering a therapeutically effective amount of a supportive care agent.

In another embodiment, the method provided herein comprises: a) administering to a patient in need thereof, a dose of about 10 mg/m$^2$-60 mg/m$^2$ of a compound or composition provided herein and b) administering a therapeutically effective amount of a supportive care agent.

The supportive care agent is any substance that treats, prevents, manages, avoids or reduces an adverse or unwanted effect from treatment with a compound or composition provided herein and is administered according to the appropriate dosing regimen for that substance. For example, different supportive care agents for treating nausea have different dosing regimens. While some are administered prophylactically, others are co-administered with a compound or composition provided herein while still others are administered after the administration of the compound or composition. Illustrative examples of supportive care agents their doses and dosing regimens are found in The Physician's Desk Reference. Some exemplary support care agents are disclosed in U.S. Application Pub. No. 2006-0025437, which incorporated by reference in its entirety.

5.7 Pharmaceutical Compositions and Dosage Forms

The methods provided herein use pharmaceutical compositions containing the compound or compositions provided herein and pharmaceutically acceptable carriers, such as diluents or adjuvants, or in combination with other active ingredients, such as another anti-cancer agent. In clinical practice, the compound or composition may be administered by any conventional route, including but not limited to orally, parenterally, rectally or by inhalation (e.g. in the form of aerosols). In one embodiment, the compound or composition is administered by an IV injection.

The pharmaceutical compositions for parenteral administration can be emulsions or homogeneous solutions. Use may be made, as solvent or vehicle, of propylene glycol, a polyethylene glycol, vegetable oils, in particular olive oil, or injectable organic esters, for example ethyl oleate. These pharmaceutical compositions can also contain adjuvants, in particular wetting, isotonizing, emulsifying, dispersing and stabilizing agents. Sterilization can be carried out in several ways, for example using a 0.2μ filter, by radiation or by heating (see, *Remington's Pharmaceutical Sciences,* 21st ed., Mack Publishing, Easton Pa. (2005). They can also be prepared in the form of sterile solid pharmaceutical compositions which can be dissolved at the time of use in sterile water or any other injectable sterile medium.

The pharmaceutical compositions can also be aerosols. For use in the form of liquid aerosols, the pharmaceutical compositions can be sterile solutions or solid pharmaceutical compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

Pharmaceutical compositions can be used in the preparation of individual, single unit dosage forms. Pharmaceutical compositions and dosage forms comprise compound and one or more excipients.

Pharmaceutical compositions and dosage forms can also comprise one or more additional active ingredients. Examples of optional second, or additional, active ingredients are disclosed herein.

In certain embodiments, the pharmaceutical composition provided herein is a a single unit dosage form. Pharmaceutical compositions and single unit dosage forms provided herein comprise a prophylactically or therapeutically effective amount of compound or composition, and typically one or more pharmaceutically acceptable carriers or excipients. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. In certain embodiments, water is a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The pharmaceutical composition or single unit dosage form, if desired, can also contain minor amounts of wetting or emulsifying agents, or pH buffering agents.

Further provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, powders and the like. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In one embodiment, the pharmaceutical compositions or single unit dosage forms are sterile and in suitable form for administration to a subject, such as an animal subject, or a mammalian subject, and such as a human subject.

A pharmaceutical composition provided herein is formulated to be compatible with its intended route of administration. Examples of routes of administration include, but are not limited to, parenteral, e.g., intravenous, intradermal, subcutaneous, intramuscular, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, intranasal or topical administration to human beings. In certain embodiments, a pharmaceutical composition is formulated in accordance with routine procedures for subcutaneous administration to human beings. In one embodiment, pharmaceutical compositions for intravenous administration are solutions in sterile isotonic aqueous buffer. Where necessary, the pharmaceutical composition may also include a solubilizing agent and a local anesthetic such as lignocamne to ease pain at the site of the injection.

Examples of dosage forms include, but are not limited to: liquid dosage forms suitable for parenteral administration to a subject; and sterile solids (e.g., crystalline or amorphous solids) that can be reconstituted to provide liquid dosage forms suitable for parenteral administration to a subject, including lyophilized solids.

The pharmaceutical composition, shape, and type of dosage forms provided herein will typically vary depending on their use. For example, a dosage form used in the initial treatment of disease may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., *Remington's Pharmaceutical Sciences*, 21st ed., Mack Publishing, Easton Pa. (2005).

Generally, the ingredients of pharmaceutical compositions provided herein are supplied either separately or mixed together in unit dosage form, for example, as a dry lyophilized powder or water free concentrate in a hermetically sealed container such as an ampoule or sachette indicating the quantity of active agent. Where the pharmaceutical composition is to be administered by infusion, it can be dispensed with an infusion bottle containing sterile pharmaceutical grade water or saline. Where the pharmaceutical composition is administered by injection, an ampoule of sterile water for injection or saline can be provided so that the ingredients may be mixed prior to administration.

In one embodiment, dosage forms provided herein comprise compound or composition within the range of about 1 mg/m$^2$ to about 150 mg/m$^2$ or about 1 mg/m$^2$ to about 75 mg/m$^2$ per day, or per week, given as a single once-a-day dose in the morning or as divided doses throughout the day taken with food. Particular dosage forms provided herein have about 1, 3, 6, 9, 12, 15, 18, 21, 24, 27 or 30 mg/m$^2$ of the compound or composition.

5.7.1 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of active ingredients. See, e.g., U.S. Pat. No. 5,134,127, which is incorporated herein by reference.

5.7.2 Topical and Mucosal Dosage Forms

In certain embodiments, provided herein are transdermal, topical, and mucosal dosage forms. Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences*, 21st ed., Mack Publishing, Easton Pa. (2005); and Introduction to Pharmaceutical Dosage Forms, 5th ed., Lea & Febiger, Philadelphia (1990). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions or dosage forms if desired. Examples of such additional ingredients are well known in the art. See, *Remington's Pharmaceutical Sciences*, 21st ed., Mack Publishing, Easton Pa. (2005).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting pharmaceutical composition.

5.8 Analytical Methods 5.8.1 Analysis of Compositions Provided Herein

The amount of N-desmethyl-SNS-595 in compositions comprising SNS-595 and N-desmethyl SNS-595, including compositions provided herein can be estimated by methods known to one of skill in the art, such as HPLC analysis. In an exemplary HPLC method, the mobile phase is water/acetonitrile (0.1% TFA) gradient, eluting from 10% to 80% acetonitrile over 30 minutes with a gradient hold from 7 to 13 minutes (26% acetonitrile). The detection is performed at 275 nm on a reverse phase column (C8).

Figure 7:
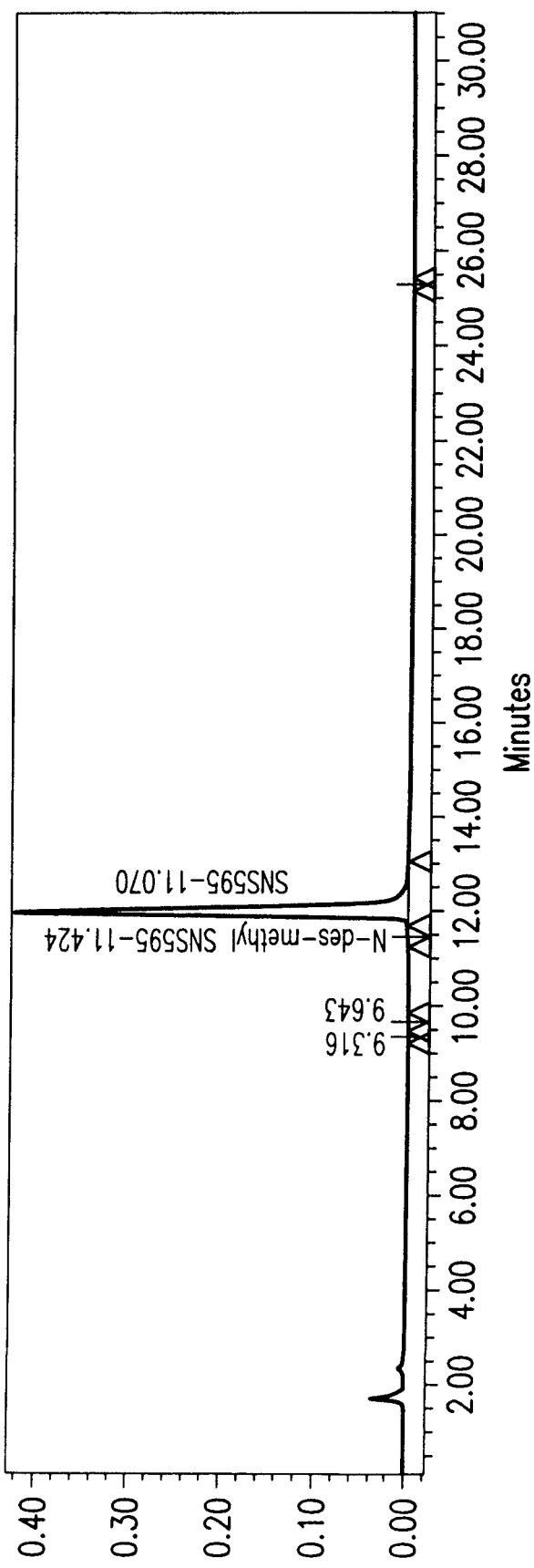

FIG. 7 provides an HPLC chromatogram of an exemplary composition comprising about 99.2% SNS-595 and about 0.6% N-desmethyl-SNS-595.

6 EXAMPLES

Certain embodiments of the claimed subject matter are illustrated by the following non-limiting examples.

Example 1

Preparation of an Exemplary Composition

A composition comprising SNS 595 and N-desmethyl-SNS-595 was prepared from (3S,4S)-3-methoxy-4-methylaminopyrrolidine di-p-toluenesulfonic acid and ethyl-7-chloro-1,4-dihydro-4-oxo-1-(2-thiazolyl)-1,8-naphthyridine-3-carboxylate. An exemplary method for preparing starting materials is provided in FIG. 2. Trans-3-benzylamino-1-tert-butyloxycarbonyl-4-hydroxypyrrolidine used in the preparation of (3S,4S)-3-methoxy-4-methylaminopyrrolidine di-p-toluenesulfonic acid was prepared as follows.

Preparation of trans-3-benzylamino-1-tert-butyloxycarbonyl-4-hydroxypyrrolidine

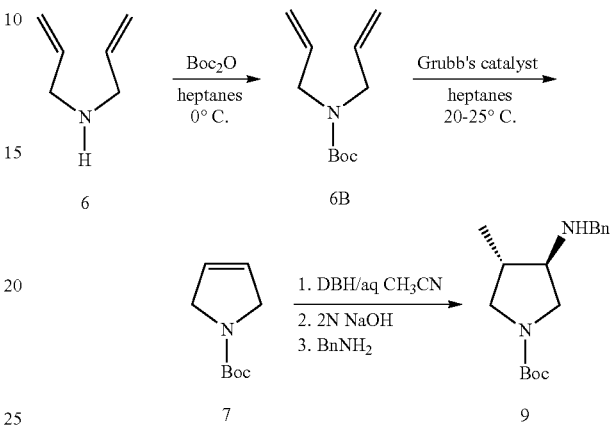

Commercially available diallylamine was reacted with di-t-butyl dicarbonate in heptane. After aqueous workup, the organic layer was further diluted with heptanes (10 vol) and azeotropically distilled to remove residual water azeotropically distilled to a known volume and the subsequent ring closing metathesis (RCM) reaction was carried by addition of Grubbs catalyst (bis(tricyclohexylphosphine)benzylidine ruthenium(IV) dichloride) in portions (0.1 mol % each, 2-3 portions) every two hours. The progress of the reaction was monitored by HPLC analysis. The mixture was quenched with 0.02 NHCL (2×5 vol). The layer was further washed with bicarbonate and water.

The ruthenium catalyst was deactivated by silica bound metal scavengers (Si-Thiol). The heptane solution containing the metathesis product 7 was concentrated to remove most of the solvent and a solvent-swap to acetonitrile (ACN) was implementated. Intermediate 7 was dissolved in 3 volumes of ACN to a cold slurry (0° C.) of dibromo dimethyl hydantoin (DBH) in 3 volumes of ACN and 1 volume of water. After reaction completion, the mixture was quenched with 10% aq. Sodium thiosulfate solution (3 volume) and extracted with ethyl acetate. The organic layer was concentrated to remove most of the solvent. Resulting bromohydrin was treated with 2 N NaOH (8 vol) to form the epoxide at ambient temperature.

The epoxide was converted to racemic 9 by treatment with benzylamine (2.5 eq) with heating to 65° C. for 14 hours. The racemic intermediate 9 precipitated out of the solution as it formed and was isolated by filtration. The crude material was reslurried in cold MTBE (10° C.). The resulting product was >99% pure.

Preparation of ethyl 1,4-Dihydro-7-[(3S,4S)-3-methoxy-4-methylamino-1-pyrrolidinyl]-4-oxo-1-(2-thiazolyl)-1,8-naphthyridine-3-carboxylate To a glass reactor covered with silver foil and equipped with an overhead stirrer was added (3S,4S)-3-methoxy-4-methylaminopyrrolidine di-p-toluenesulfonic acid (1190 g) and acetonitrile (9.0 L), and the mixture stirred. The solution was cooled and triethylamine (TEA) (1560 mL) was added, maintaining the batch temperature below 5° C. Ethyl-7-chloro-1,4-dihydro-4-oxo-1-(2-thiazolyl)-1,8-naphthyridine-3-carboxylate (750 g) was added, the ice-bath was removed and the reaction temperature allowed to rise and then stirred an additional 48 hours. The reaction was filtered, the filter cake was washed with acetonitrile (3×800 mL), and dried in vacuo to afford 936 g of the title compound as a white solid (97.6%).

Before working up the reaction, HPLC analysis of the reaction mixture (as described in section 5.4.1) was conducted to ensure that intermediate ethyl-7-chloro-1,4-dihydro-4-oxo-1-(2-thiazolyl)-1,8-naphthyridine-3-carboxylate was <0.7%.

Preparation of a composition comprising 1,4-Dihydro-7-[(3S,4S)-3-methoxy-4-methylamino-1-pyrrolidinyl]-4-oxo-1-(2-thiazolyl)-1,8-naphthyridine-3-carboxylate and N-desmethyl 1,4-Dihydro-7-[(3S, 4S)-3-methoxy-4-methylamino-1-pyrrolidinyl]-4-oxo-1-(2-thiazolyl)-1,8-naphthyridine-3-carboxylate To a glass reactor covered with silver foil and equipped with an overhead stirrer and a heating mantel was added ethyl 1,4-Dihydro-7-[(3S,4S)-3-methoxy-4-methylamino-1-pyrrolidinyl]-4-oxo-1-(2-thiazolyl)-1,8-naphthyridine-3-carboxylate (936 g), 1 N aqueous NaOH (3463) mL) and EtOH (112 mL) and the suspension stirred. The reaction was adjusted to pH 7.5 with 25% acetic acid (660 mL), heated to 60° C. for approximately 2 hours, and then allowed to cool. The resulting solids were filtered, washed with water (2×1498 mL) and EtOH (3×1498 mL), and dried in vacuo. The product was transferred to a glass reactor equipped with an overhead stirrer, heating mantle and water filled condenser, and then diluted with EtOH (anhydrous; 16.8 L). The suspension was heated to 80° C. for approximately 3 hours, allowed to cool, and the solids filtered, washed with EtOH (anhydrous; 3×1498 mL) and dried in vacuo to afford 726 g of the composition comprising 99.2% 1,4-Dihydro-7-[(3S,4S)-3-methoxy-4-methylamino-1-pyrrolidinyl]-4-oxo-1-(2-thiazolyl)-1,8-naphthyridine-3-carboxylate (SNS 595) and 0.8% N-desmethyl 1,4-dihydro-7-[(3S,4S)-3-methoxy-4-methylamino-1-pyrrolidinyl]-4-oxo-1-(2-thiazolyl)-1,8-naphthyridine-3-carboxylate (N-desmethyl-SNS-595) as white solid (86.3%).

Example 2

Preparation and characterization of a hydrate of SNS-595

Methods of Preparation

The starting material, ethyl 1,4-dihydro-7-[(3S,4S)-3-methoxy-4-methylamino-1-pyrrolidinyl]-4-oxo-1-(2-thiazolyl)-1,8-naphthyridine-3-carboxylate, was prepared according to the reaction scheme depicted in FIG. 2. To a glass reactor covered with silver foil and equipped with an overhead stirrer and a heating mantel was added ethyl 1,4-dihydro-7-[(3S,4S)-3-methoxy-4-methylamino-1-pyrrolidinyl]-4-oxo-1-(2-thiazolyl)-1,8-naphthyridine-3-carboxylate (2685 g), 1 N aqueous NaOH (9935 mL) and EtOH (180 mL), and the resulting suspension was stirred. The reaction was adjusted to pH 7.5 with 25% acetic acid (660 mL), heated to 60° C. for approximately 2 hours, and then allowed to cool. The resulting solids were filtered, washed with water (2×4296 mL) and EtOH (3×4296 mL), and dried in vacuo at ambient temperature to give SNS-595 hydrate (2054 g).

Alternative Methods of Preparation

Other methods of preparation of this hydrate of SNS-595 may include, e.g.: dissolution of SNS-595 in water or an organic/water solvent system followed by precipitation of this hydrate of SNS-595; slurry of a solid form of SNS-595 in water or an organic/water solvent system followed by transformation to this hydrate of SNS-595; and exposure of a solid form of SNS-595 to humidity, heat and/or reduced pressure, thereby forming this hydrate of SNS-595.

Methods of Characterization

X-Ray Powder Diffraction (XRPD) Analysis

XRPD patterns were obtained on a Scintag $X_2$ θ/θ diffractometer operating with copper radiation at 45 kV and 40 mA, using a Thermo ARL Peltier-cooled solid-state detector. Source slits of 2 and 4 mm, and detector slits of 0.5 and 0.3 mm, were used for data collection. Unmilled material was placed in a stainless steel sample holder, leveled using a glass microscope slide, and scanned on a six-position auto-sampler. Powder diffraction patterns of the samples were obtained from 2° to 42° 2θ at 1°/min. Calibration of the diffractometer was verified using a silicon powder standard. Raw data files were converted to ACS II format, transferred to a computer and displayed in Origin® 6.1 for Windows.

Differential Scanning Calorimetry (DSC) Analysis

DSC measurements were collected using a PerkinElmer Pyris 1 DSC system equipped with an Intracooler 2P refrigeration unit. The Pyris 1 DSC was purged with nitrogen. Calibration was performed prior to analysis using an Indium standard at a 10° C./min heating rate. Approximately 2 mg samples were individually placed in tared PerkinElmer 25-µL universal aluminum pans with holes in the lids. The samples were weighed on a Sartorius microbalance and sealed using a PerkinElmer pan crimper press. Samples were heated from approximately 25° C. to approximately 350° C. at approximately 10° C./min.

Thermogravimetric Analysis (TGA)

TGA measurements were collected using a PerkinElmer TGA 7 purged with nitrogen. A 100-mg standard weight and nickel sample were used to verify balance and temperature calibrations, respectively. Samples were heated from approximately 25° C. to approximately 350° C. at approximately 10° C./min.

Water Content Analysis

The amount of water in a hydrate may be analyzed using a number of techniques as understood in the art. For example, the amount of water may be determined based on the observed weight loss in a TGA thermogram. In addition, the exhaust from a TGA furnace may be coupled to an instrument of chemical analysis, such as an mass spectrometry instrument or an infrared spectroscopy instrument, to confirm the chemical purity of the water vapor emitted upon heating. Moreover, Karl Fischer (KF) analysis may be used to analyze the water content of a hydrate sample. Coulometric KF analysis for water determination may be performed using a Mettler Toledo DL39 Karl Fischer titrator. Approximately 14-32 mg of a sample is placed in the KF titration vessel containing HYDRANAL®—Coulomat AD reagent for coulometric KF titration and mixed for 60 seconds to ensure dissolution. The sample is then titrated by means of a generator electrode which produces iodine by electrochemical oxidation. The analysis is repeated to ensure reproducibility of the measurements.

Characterization

Figure 8:
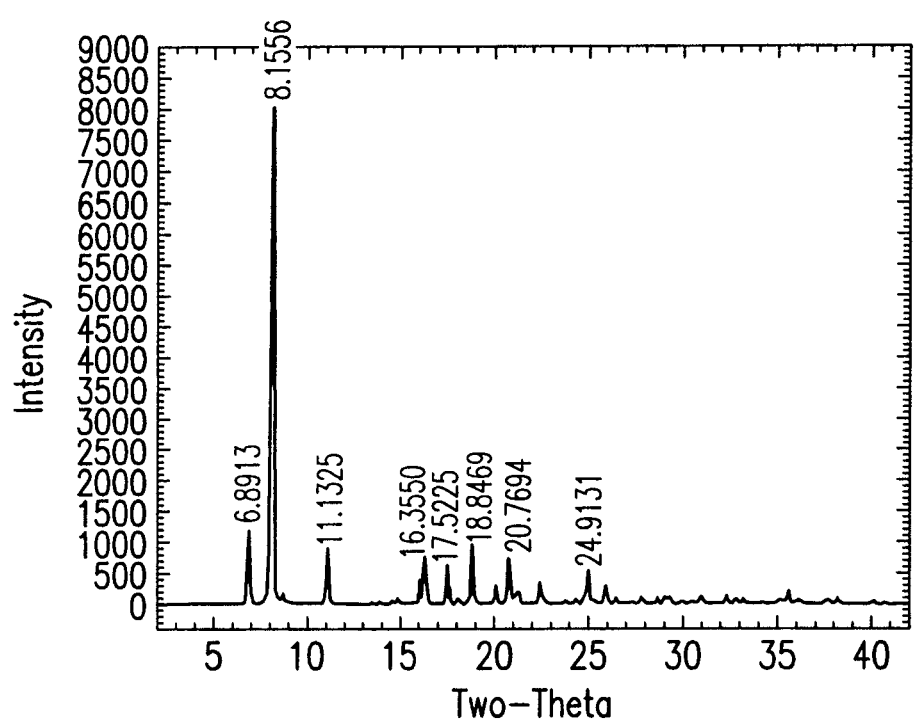
FIG. 8 shows an x-ray powder diffraction (XRPD) pattern (measured using Cu Kα radiation) for a hydrate of SNS-595.

A hydrate of SNS-595 was characterized by X-ray powder diffraction (XRPD) using the methods described above. A representative XRPD pattern of this hydrate of SNS-595 is shown in FIG. 8. The 2θ angles (Cu Kα radiation), D-spacing values and relative intensities for certain XRPD peaks of this hydrate of SNS-595 are provided in Table 1.

TABLE 1

| Approximate Peak Position (in Degrees 2θ) | Approximate Peak Position (in D-spacing in Å) | Relative Peak Intensity (as percentage of maximum peak intensity) |
|---|---|---|
| 6.8913 | 12.8164 | 15.21 |
| 8.1556 | 10.8321 | 100.00 |
| 11.1325 | 7.9413 | 11.17 |
| 16.3550 | 5.4154 | 9.45 |
| 17.5225 | 5.0571 | 7.75 |
| 18.8469 | 4.7046 | 11.84 |
| 20.7694 | 4.2733 | 9.15 |
| 24.9131 | 3.5711 | 6.70 |

Figure 9:
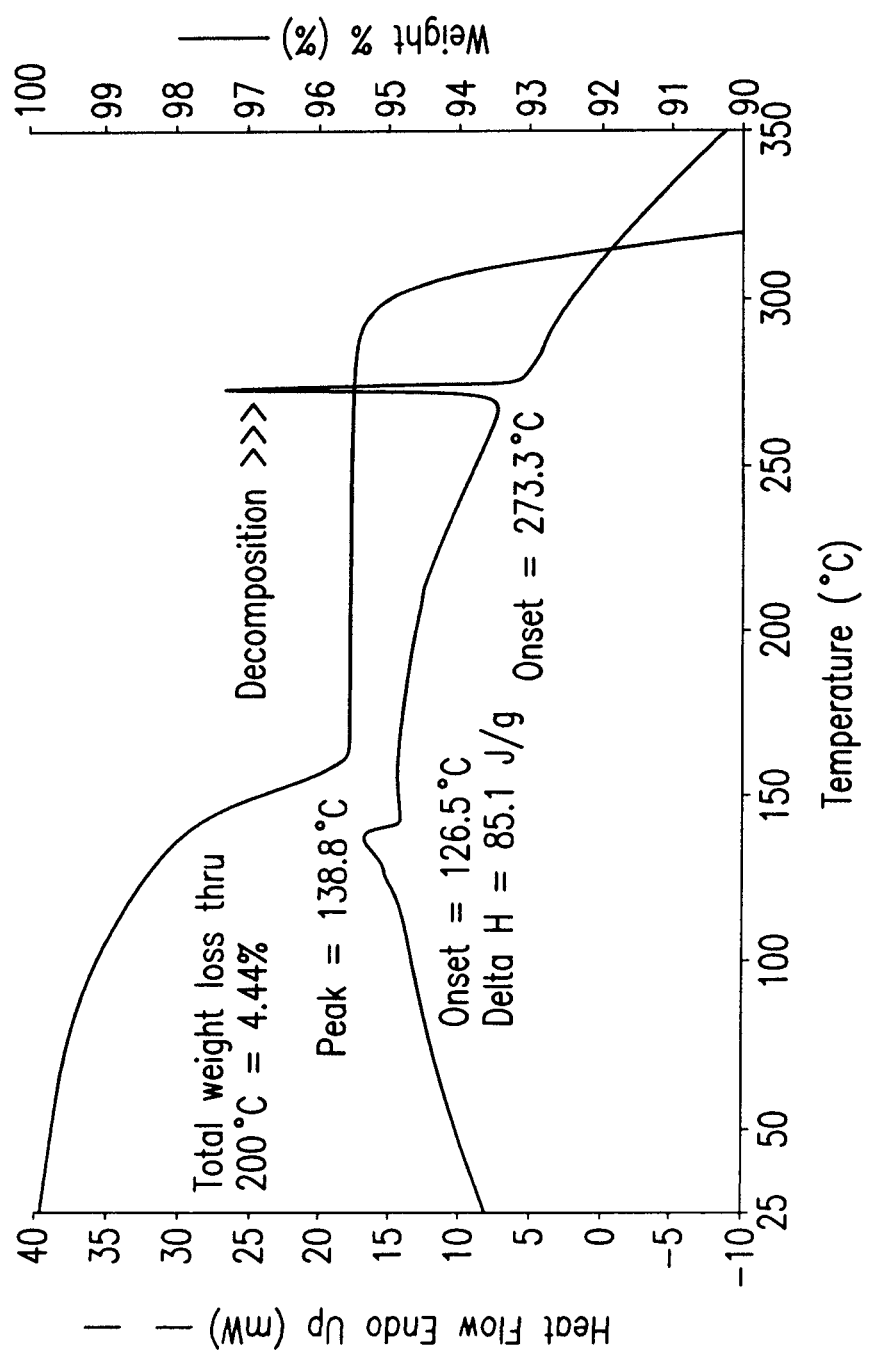
FIG. 9 shows a differential scanning calorimetry (DSC) and thermal gravimetric analysis (TGA) thermogram for a hydrate of SNS-595.

The hydrate of SNS-595 was also characterized by thermogravimetric analysis and differential scanning calorimetry, using the methods described above. Representative TGA and DSC thermograms are shown in FIG. 9. The TGA thermogram exhibited a weight loss of approximately 4.44% between the temperatures of approximately 25° C. and approximately 200° C. The DSC thermogram exhibited an endothermic event with an onset temperature of approximately 126.5° C., a peak temperature of approximately 138.8° C., and a heat of fusion of approximately 85.1 J/g. The DSC thermogram also exhibited an endothermic event with an onset temperature of approximately 273.3° C.

Total water content in particular samples of this hydrate of SNS-595 include values ranging between: 0.8 to 1.2 molar equivalents of water per mole of SNS-595; 0.9 to 1.1 molar equivalents of water per mole of SNS-595; 0.95 to 1.05 molar equivalents of water per mole of SNS-595; and 0.98 to 1.02 molar equivalents of water per mole of SNS-595.

Example 3

Pharmaceutical Composition Suitable for Injection or Intravenous Infusion

An illustrative example of a suitable pharmaceutical composition comprises:

10 mg total SNS-595 and N-desmethyl-SNS-595 per mL of aqueous solution of 4.5% sorbitol that is adjusted to pH 2.5 with methanesulfonic acid. One protocol for making such a solution includes the following for making a 100 mg/10 mL presentation: 100 mg total SNS-595 and N-desmethyl-SNS-595 (about 99.2 mg SNS-595 and about 0.8 mg N-desmethyl-SNS-595) and 450 mg D-sorbitol are added to distilled water; the volume is brought up to a volume of 10 mL; and the pH of the resulting solution is adjusted to 2.5 with methanesulfonic acid. The resulting composition is also suitable for lyophilization. The lyophilized form is then reconstituted with sterile water to the appropriate concentration prior to use.

Example 4

Pharmaceutical Composition Suitable for Injection or Intravenous Infusion

An illustrative example of a suitable pharmaceutical composition comprises: 10 mg total SNS-595 and N-desmethyl-SNS-595 per mL of aqueous solution of 4.5% sorbitol that is adjusted to pH 2.5 with methanesulfonic acid. One protocol for making such a solution includes the following for making a 100 mg/10 mL presentation: 100 mg total SNS-595 and N-desmethyl-SNS-595 (about 98.5 mg SNS-595 and about 1.5 mg N-desmethyl-SNS-595) and 450 mg D-sorbitol are added to distilled water; the volume is brought up to a volume of 10 mL; and the pH of the resulting solution is adjusted to 2.5 with methanesulfonic acid. The resulting composition is also suitable for lyophilization. The lyophilized form is then reconstituted with sterile water to the appropriate concentration prior to use.

Example 5

Comparative cytotoxicity of SNS-595, N-desmethyl-SNS-595 and O-desmethyl-SNS-595 in MTT Assay Preparation of Samples Stock Solutions MTT Dye Solution: 5 mg/mL MTT dye (Sigma #M2128) in sterile PBS, filter sterilized, stored at 4° C. in a dark bottle no longer than 1 month. Lysis Buffer: 50% N,N-dimethyl formamide (Aldich #31, 993-7) in dH$_2$0, 20% w/v lauryl sulfate (added with stirring at 37° C.) (Sigma #L4509), adjusted pH to 4.7 with 2.5% of 80% acetic acid (Fisher #A490-212) and 2.5% 1 N HCl (Spectrum #HY105).

Supplemented RPMI media: 500 mL RPMI (Cellgro #10-040-CV), 10% FBS (Cellgro #35-011CV) and 1% Sodium Bicarbonate solution (Cellgro @35-035-CI), 1% Antibotic Solution (100x stock; Cellgro #30-004CI).

Trypsin (Cellgro #25-053-CL)

Cells

HCT-116 cells were purchased from ATTC (#CCL-247).

Controls

Background: No cells, Totals: Cells treated with DMSO only

Method 96-well tissue culture-treated flat bottom plates (Costar #3595) were plated with 4000 trypsinized cells in 100 μL/well and incubated overnight. 100x stock concentrations of compounds were prepared in DMSO and serially diluted two-fold in DMSO in a 96-well polypropylene v-bottom plate (Costar #3363). 5 μL of DMSO dilutions were then added to 45 μL supplemented RPMI, and 10 μL/well of this mixture were added to plates containing HCT-116 cells. The highest concentration of compounds was 5 μM. Plates were incubated for 72 hours at 37° C. in an incubator (5% CO$_2$).

After incubation, 204 of MTT solution were added to each well and incubated at 37° C. for 1.5 hour. 100 μL lysis buffer was then added and plates were incubated for 48 hours at 37° C. Cell viability was then recorded by absorbance at 595 nm using a Biorad Benchmark Microplate Reader. The fraction of dead cells was determined by Fraction of Dead cells=Absorbance of sample well−Avg(no cell control)/Avg(Absorbance of DMSO only Control)−Avg(no cell control).

The results of the cell viability assay are shown in FIG. 1. SNS-595 reduced cell viability with an IC$_{50}$=425 nM in this assay. N-desmethyl-SNS-595 has an IC$_{50}$=507 nM. O-desmethyl-SNS-595 has an IC$_{50}$>>5 μM.

Example 7

Identification of N-desmethyl SNS-595

The in vitro production of N-Desmethyl SNS-595 from SNS-595 was monitored as described herein. The pooled Human Liver Microsomes were obtained from BD Gentest and NADPH was obtained from Sigma.

The in vitro reactions were performed (a) in the presence of NADPH as a cofactor and (b) in the absence of NADPH to identify any SNS-595 derivatives generated by cofactor independent mechanisms.

The reaction mixture constituted 100 mM Sodium Phosphate buffer, pH 7.4, containing 3.3 mM $MgCl_2$, 1 mg/mL liver microsomal protein, 10 or 100 µM SNS-595, and 1 mM NADPH for reaction with NADPH. In both the NADPH plus and minus reactions, SNS-595 was added to the reaction mixture and allowed to equilibrate to 37° C. for 10 minutes before starting the reaction by adding NADPH or an equivalent volume of buffer. Reactions were performed in a volume of 1 mL in 2 mL 96-well polypropylene assay blocks. The reaction was stopped by adding an equal volume of acetonitrile at both 0 and 60 minutes after initiating the reaction. Samples were placed on ice until centrifugation at 4100 g for 10 minutes to remove proteins for subsequent analysis.

Analysis

SNS-595 and the reaction products were identified on an API 4000 mass spectrometer coupled to a turbo electro spray ionization source. Prior to MS analysis chromatography was performed to achieve separation of the reaction precuts (N-desmethyl-SNS-595 had the same retention time as SNS-595). The HPLC system consisted of an Agilent 1100 binary pump and single wavelength UV/Vis as a detector, and a Phenomenex Synergi Hydro-RP column (150×2 mm, 4 micron, 80 Å particle size). Following column separation, UV spectra were collected at 350 nm before mass spectral analysis. Mass spectral identification of the reaction products was done using a series of three experiments; MS full scan, product ion scans on all reaction products identified in the MS full scan analysis as well as multiple reaction monitoring (MRM) or product ion scans on theoretically possible reaction products. Product ion scans were performed at collision energies of 50 volts for SNS-595 and the reaction products.

N-desmethyl SNS-595 and O-desmethyl SNS-595 were synthesized. Retention time and fragmentation pattern of the authentic standards was compared with those of the reaction product peaks and used to verify the identity of the products of the in vitro reaction.

Results

Figure 3A:
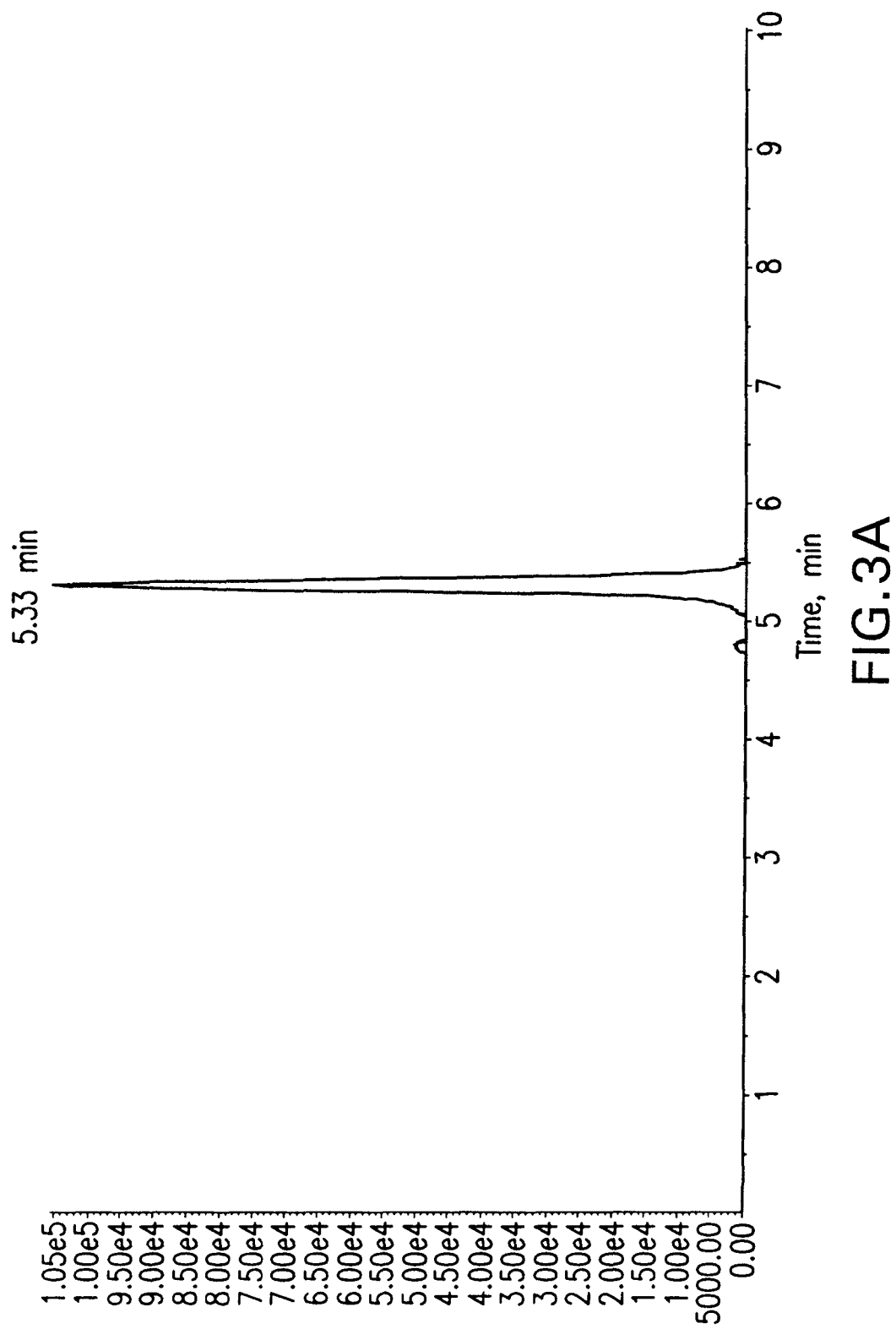

Identification of the N-desmethyl SNS-595 was based on a comparison of retention time and fragmentation patterns with those of the chemically synthesized N-desmethyl reference standard. As shown in FIG. 3, N-desmethyl-SNS-595 (peak 2) is the predominant product formed. At a 10 µM incubation concentration, N-desmethyl-SNS-595 is the only product detectable. The second product formed after incubation of high concentrations of SNS-595 was identified as O-desmethyl-SNS-595 (peak 1 in FIG. 3). N-desmethyl SNS-595 has a retention time of 5.33 min and is chromatographically separated from peak 1 in both chromatograms in FIG. 3 (4.79 min; small peak seen in pane A not visible in pane B at the scale shown).

Figure 4:
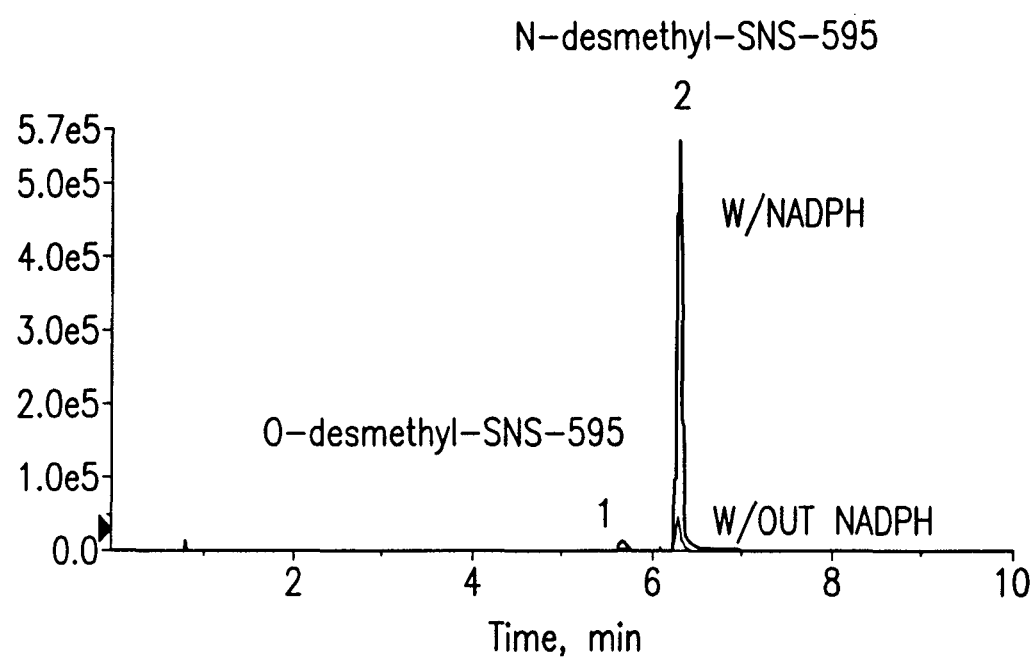

Chromatographic identification of peak 2 as N-desmethyl SNS-595 (retention time 5.33 min) is shown in FIG. 4. The retention time of compounds corresponding to peak 2 is the same as the chemically synthesized standard of N-desmethyl SNS-595, shown in pane B. Peak 2 is also resolved from the O-desmethyl SNS-595 which has a retention time 4.79 min. Confirmation of O-desmethyl SNS-595 was made through comparison with a chemically synthesized reference compound.

Figure 5:
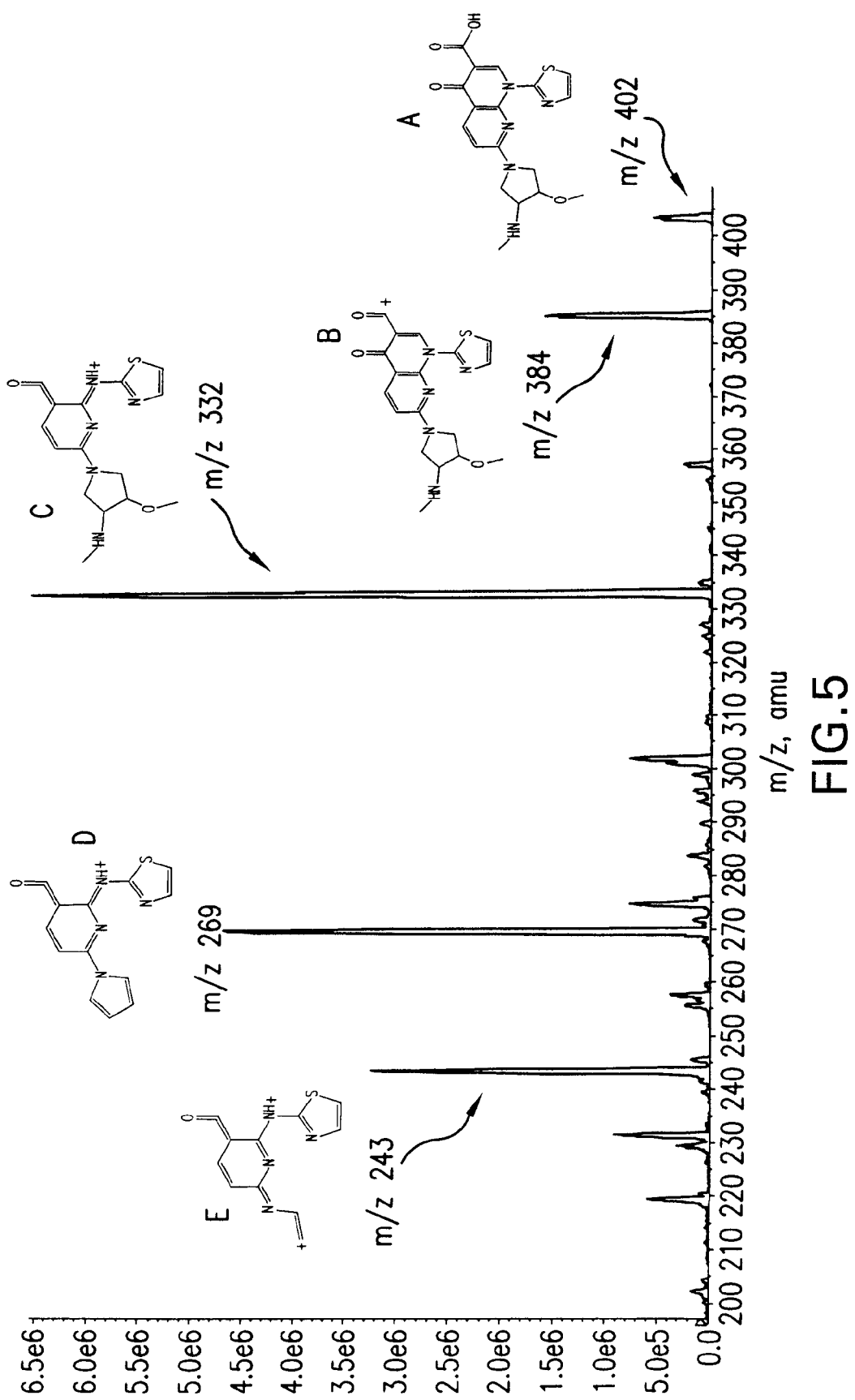

Mass spectra identification of peak 1 and 2 as demethylated products of SNS-595 was made by comparison between the product ion spectra of SNS-595 and peaks 1 and 2. FIG. 5 shows the product ion spectra of SNS-595 with structures assigned to the predominant m/z fragments. In FIG. 5, structure A is SNS-595 and structures B and C are assigned to fragmentation on the carboxylic acid region of the molecule having a mass loss of 18 and 70 amu, respectively. Structure D is assigned to the m/z 269 fragment, which does not contain the 3-methoxy or 4-methylamino moieties of the pyrrolidinyl ring. Structure E also lacks the 3-methoxy and 4-methylamino pieces and is assigned to m/z 243.

Figure 6:
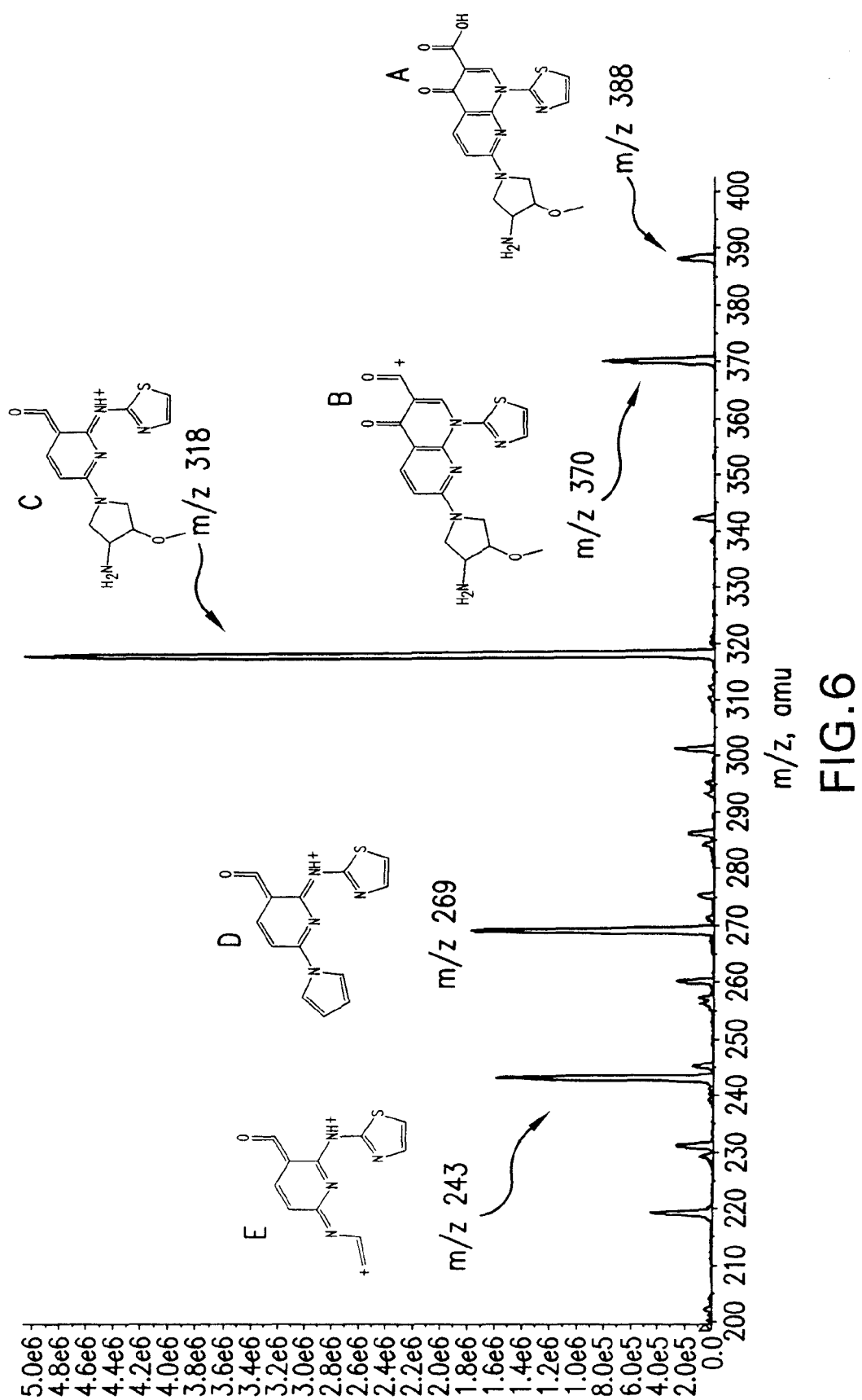

FIG. 6 is the spectra from peak 2 with structures A-E assigned to the major fragments (spectra from the authentic reference N-desmethyl SNS-595 standard is identical). Structure A and fragments B, and C show the same delta mass loss as fragments B and C in the SNS-595 spectra, indicating peak 2 is structurally similar to SNS-595. In addition, structures A, B, and C have a mass of 14 amu less than the corresponding fragments from the SNS-595 spectra indicating a loss of a methyl group. Structures D and E share the same mass fragments in both the spectra for peak 2 and SNS-595 showing the loss of 14 amu results from N-demethylation.

The embodiments of the claimed subject matter described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

What is claimed is:

1. A pharmaceutical composition comprising a hydrate of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and a pharmaceutically acceptable carrier, excipient or adjuvant, wherein the hydrate exhibits an X-ray powder diffraction pattern comprising a peak at approximately 8.2 degrees 2θ, and the composition is for oral administration.

2. The pharmaceutical composition of claim 1, wherein the hydrate exhibits an X-ray powder diffraction pattern further comprising peaks at approximately 6.9, 11.1 and 18.8 degrees 2θ.

3. The pharmaceutical composition of claim 2, wherein the hydrate exhibits an X-ray powder diffraction pattern further comprising peaks at approximately 16.4, 17.5, 20.8 and 24.9 degrees 2θ.

4. The pharmaceutical composition of claim 2, wherein the hydrate has an X-ray powder diffraction pattern substantially similar to FIG. 8.

5. A pharmaceutical composition comprising a hydrate of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and a pharmaceutically acceptable carrier, excipient or adjuvant, wherein the hydrate comprises between approximately 0.8 and 1.2 molar equivalents of water per mole of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, and wherein the composition is for oral administration.

6. The pharmaceutical composition of claim 5, wherein the hydrate comprises between approximately 0.9 to 1.1 molar equivalents of water per mole of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid.

7. The pharmaceutical composition of claim 5, wherein the hydrate comprises between approximately 0.95 to 1.05 molar equivalents of water per mole of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid.

8. The pharmaceutical composition of claim 5, wherein the hydrate comprises between approximately 0.98 to 1.02 molar equivalents of water per mole of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid.

* * * * *